(12) United States Patent
Berggren et al.

(10) Patent No.: US 7,601,687 B2
(45) Date of Patent: Oct. 13, 2009

(54) MECHANISM FOR IDENTIFYING DRUGS FOR THE TREATMENT OF TYPE II DIABETES

(75) Inventors: Per-Olof Berggren, Solna (SE); Barbara Leibiger, Solna (SE); Ingo Leibiger, Solna (SE)

(73) Assignee: BioCrine AB, Stockholm (SE)

( * ) Notice: Subject to any disclaimer, the term of this patent is extended or adjusted under 35 U.S.C. 154(b) by 15 days.

(21) Appl. No.: 11/492,530

(22) Filed: Jul. 25, 2006

(65) Prior Publication Data

US 2007/0003532 A1    Jan. 4, 2007

(51) Int. Cl.
*A61K 38/00* (2006.01)
*A61K 38/28* (2006.01)
*C12P 21/06* (2006.01)
*C12N 5/00* (2006.01)
*C12N 5/06* (2006.01)
*C12N 15/00* (2006.01)

(52) U.S. Cl. .................. 514/2; 435/69.1; 435/320.1; 435/325; 435/326; 435/373; 435/375; 435/455; 514/3

(58) Field of Classification Search .................. None
See application file for complete search history.

(56) References Cited

OTHER PUBLICATIONS

Watada et al Bunshi Tonyobyogaku 7:165-176, 1996.*
Uhles et al. Isoform-specific insulin receptor signaling involves different plasma membrane domains J Cell Biol. 163(6):1327-37, 2003.*
Berggren, P.O., and Larsson, O. (1994) Ca2+ and Pancreatic B-Cell Function; Biochem Soc. Trans. 22, 12-18.
Ebina, Y., Ellis, L., Jarnagin, K., Edery, M., Graf, L., Clauser, E., Ou, J.H., Masiarz, F., Kan, Y.W., Goldfine, I.D., Roth, R.A., and Rutter, W.J. (1985); The Human Insulin Receptor cDNA: The Structural Basis for Hormone-Activated Transmembrane Signalling. Cell 40, 747-758.
Flier, J.S. (1996) Chapter 15; The Insulin Receptor, Diabetes Mellitus, Lippincott-Raven Publishers, Philadelphia.
Herz, J., and Gerard, R.D. (1993); Adenovirus-Mediated Transfer of Low Density Lipoprotein Receptor Gene Acutely Accelerates Cholesterol Clearance in Normal Mice.; Proc. Natl. Acad. Sci. USA 90, 2812-2816.
Kulkami, R.N., Bruning, J.C., Winnay, J.N., Postic, C., Magnuson, M.A., and Kahn, C.R., (1999); Tissue-Specific Knockout of the Insulin Receptor in Pancreatic Cells Creates an Insulin Secretory Defect Similar to that of Type 2 Diabetes; Cell 96, 329-339.
Leibiger, I.B., Walther, R., Pett, U., and Leibiger, B. (1994a); Positive and Negative Regulatory Elements are Involved in Transcriptional Control of the Rat Glucokinase Gene in the Insulin Producing Cell Line HIT-M2.2.2 FEBS Letters 337, 161-166.
Leibiger, B., Walther, R., Leibiger, I.B. (1994b); The Role of the Proximal CTAAT-Box of the Rat Glucokinase Upstream Promoter in Transcriptional Control in Insulin-Producing Cells. Biol. Chem. Hoppe-Seyler 375, 93-98.

Leibiger, I.B., Leibiger, B., Moede, T., and Berggren, P.O. (1998a); Exocytosis of Insulin Promotes Insulin Gene Transcription Via the Insulin Receptor/PI-3 Kinase/p70 s6 Kinase and CaM Kinase Pathways. Mol. Cell 1, 933-938.
Leibiger, I.B., and Berggren, P.O. (1998b); Short-term Regulation of Insulin Gene Transcription by Glucose; Proc. Natl. Acad. Sci., USA 95, 9307-9312.
Leibiger, B., Wahlander, K., Berggren, P.O., and Leibiger, I.B. (2000); Glucose-stimulated Insulin Biodynthesis Depends on Insulin-Stimulated Insulin Gene Transcription; J. Biol. Chem. 275, 30153-30156; JBC Published Jul. 25, 2000 as 10.1074/jbc. M005216200.
Moede, T., Leibiger, B., Pour, H.G., Berggren, P.O., and Leibiger, I.B. (1999); Identification of a Nuclear Localization Signal, RRMKWKK, In the Homeodomain Transcription Factor PDX-1. FEBS Letters 461, 229-234.
Moitoso de Vargas, L., Sobolewski, Jr., Siegel, R., and Moss, L.G. (1997); Individual Cells Within the Intact Islet Differently Respond to Glucose.; J. Biol. Chem. 272, 26573-26577.
Russell, P.R. (1985); Gene 40, pp. 125-130.
Sambrook, J., Fritsch, E.F., Maniatis, T., (1989); Molecular Cloning, A Laboratory Manual Second Edition; Cold Spring Harbor Laboratory Press.
Sharma, A., Fusco-DeMane, D., Henderson E., Efrat, S. and Stein, R. (1995); The Role of the Insulin Control Element and RIPE3b1 Activators in Glucose-Stimulated Transcription of the Insulin Gene; Mol. Endocrinol. 9, 1468-1476.
Taylor, S.I. (1999); Deconstructing Type 2 Diabetes; Cell 97, 9-12.
Ullrich, A., Bell, J.R., Chen E.Y., Herrera, R., Petruzzelli, L.M., Dull, TJ., Gray, A., Coussens, L., Liao, Y.C., Tsubokawa, M. Mason, A., Seeburg, P.H., Grunfeld, C., Rosen, O.M., and Ramachandran, J. (1985); Human Insulin Receptor and Its relationship to the Tyrosine Kinase Family of Oncogenes; Nature 313, 756-761.
Wang X, Appukuttan B, Ott S., Patel R., Irvine J., Song J., Park JH, Smith R, Stout JT (2000) Efficient and Sustained Transgene Expression in Human Corneal Cells Mediated by a Lentiviral Vector; Gene Ther, Feb; 7(3)196-200.

(Continued)

*Primary Examiner*—Sumesh Kaushal
(74) *Attorney, Agent, or Firm*—McDonnell Boehnen Hulbert & Berghoff LLP

(57) ABSTRACT

Insulin resistance is a central feature of type II diabetes and other diseases, and may affect every tissue of the body, including the pancreatic beta cell. Insulin signaling is mediated by a complex network of diverging and converging pathways, with alternative proteins and isoforms at almost every step in the process. We have previously shown that insulin activates the transcription of its own gene by signaling through Insulin Receptor A type (Ex11−), PI3 kinase and p70 s6 kinase. When studying the mechanisms underlying the glucose-stimulated activation of the glucokinase gene in pancreatic beta cells, we now demonstrate that also here secreted insulin is a key-factor. In contrast to the insulin gene, transcription of the glucokinase gene is promoted by signaling via Insulin Receptor B type (Ex11+) and protein kinase B (c-Akt). These data provide the first evidence for selectivity in insulin action via the two isoforms of the Insulin Receptor, A type (Ex11−) and B type (Ex11+), and reinforce the concept of the beta cell being an important target of insulin action.

11 Claims, 18 Drawing Sheets

OTHER PUBLICATIONS

Figures 2A, 2B, 2C:
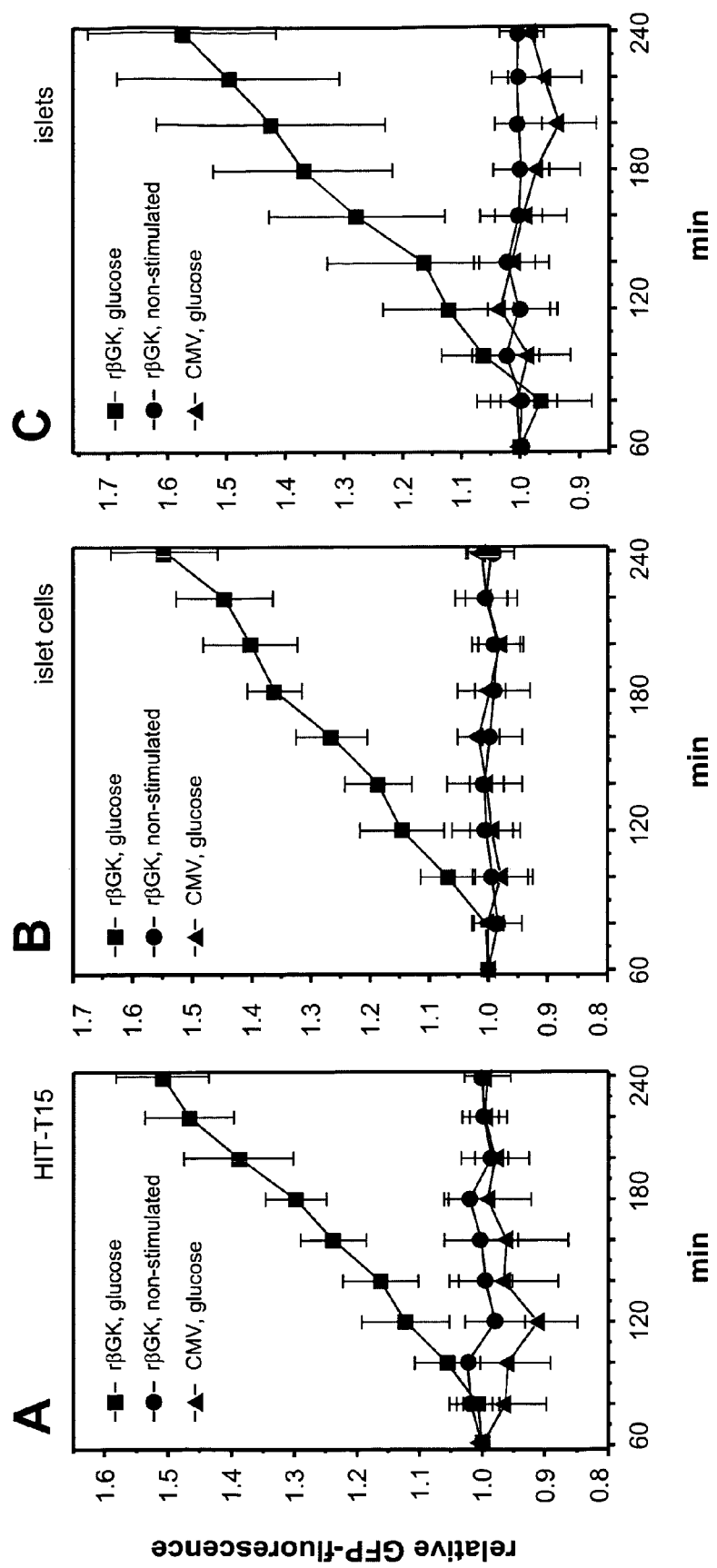

Watada, H., Kajimoto, Y., Umayahara, Y., Matsuoka, T., Kaneto, H., Fujitani, Y., Kamada, T., Kawamori, R., and Yamasaki, Y. (1996); The Human Glucokinase Gene Beta-Cell-Type Promoter: An Essential Role of Insulin Promoter Factor 1/PDX-1 in Its Activation in HIT-T15 Cells; Diabetes 45; 1478-1488.

White, M.F., and Kahn, C.R., (1994); The Insulin Signaling System; J. Biol. Chem. 269; 1-4.

Leibiger, B., Leibiger, I.B., Moede, T., Kemper, S., Kulkarni, R., Kahn, C.R., Moltoso de Vargas, L. and Berggren, P-0. (2001); Selective Insulin Signaling Through A and B Insulin Receptors Regulates Transcription of Insulin and Glucokinase Genes in Pancreatic β Cells. Molecular Cell; vol. 7, 559-570.

Leibiger, I.B., Leibiger, B., Moede, T. and Berggren, P-O. (1998) Exocytosis of Insulin Promotes Insulin Gene Transcription Via the Insulin Receptor/PI-3 Kinase/p70 s6 Kinase and CaM Kinase Pathways. Molecular Cell, vol. 1, 933-938.

Leibiger, B., Wahlander, K., Berggren, P-O. and Leibiger, B.I. (2000) Glucose-stimulated Insulin Biosynthesis Depends on Insulin-stimulated Insulin Gene Transcription. The Journal of Biological Chemistry vol. 275, No. 39.

Aspinwall, C.A., Lakey, J.R.T. and Kennedy, R.T. (1999) Insulin-stimulated Insulin Secretion in Single Pancreatic Beta Cells. The Journal of Biological Chemistry vol. 274, No. 10.

Leibiger, B., Moede, T., Uhles, S., Berggren P.-O., Leibiger, I.B., Short-term Regulation of Insulin Gene Transcription; Biochemical Society Transactions (2002); vol. 30, part 2; pp. 312-318.

Taha, C., Klip, A.; The Insulin Signaling Pathway (1999); The Journal of Membrane Biology 169, Topical Review; pp. 1-12.

Levy-Toledano, R., Caro, L.H.P., Accili, D. and Taylor, S.I.; Investigation of the Mechanism of the Dominant Negative Effect of Mutations in the Tyrosine Kinase Domain of the Insul Receptor (1994); The EMBO Journal, vol, 13, No. 4; pp. 835-842.

* cited by examiner

FIGURE 1A -D
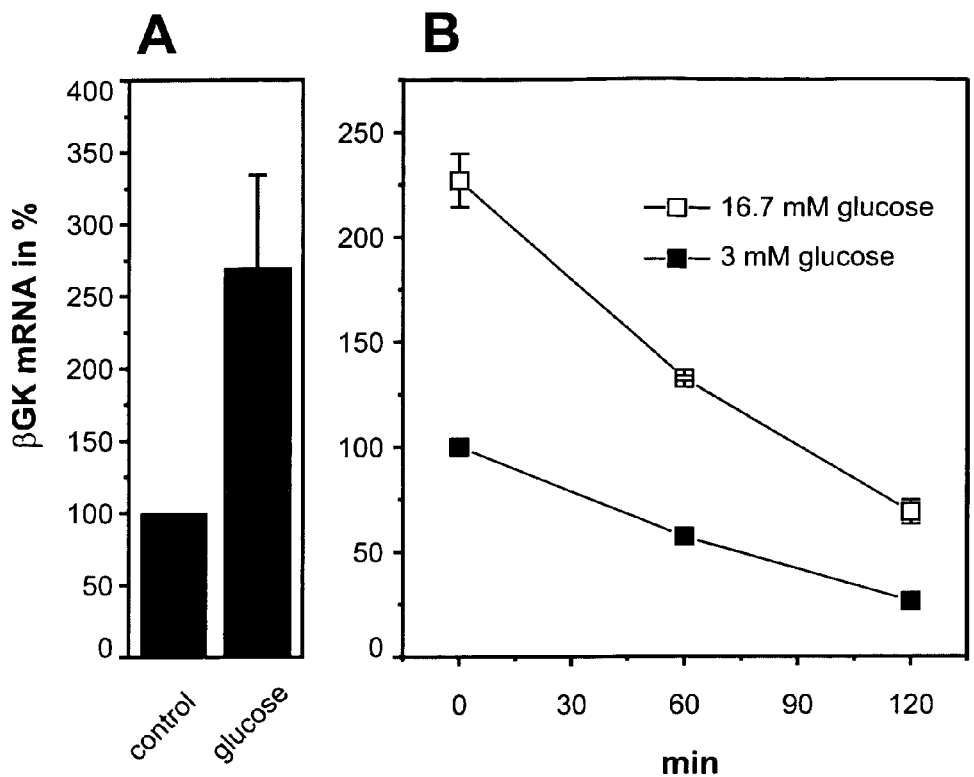
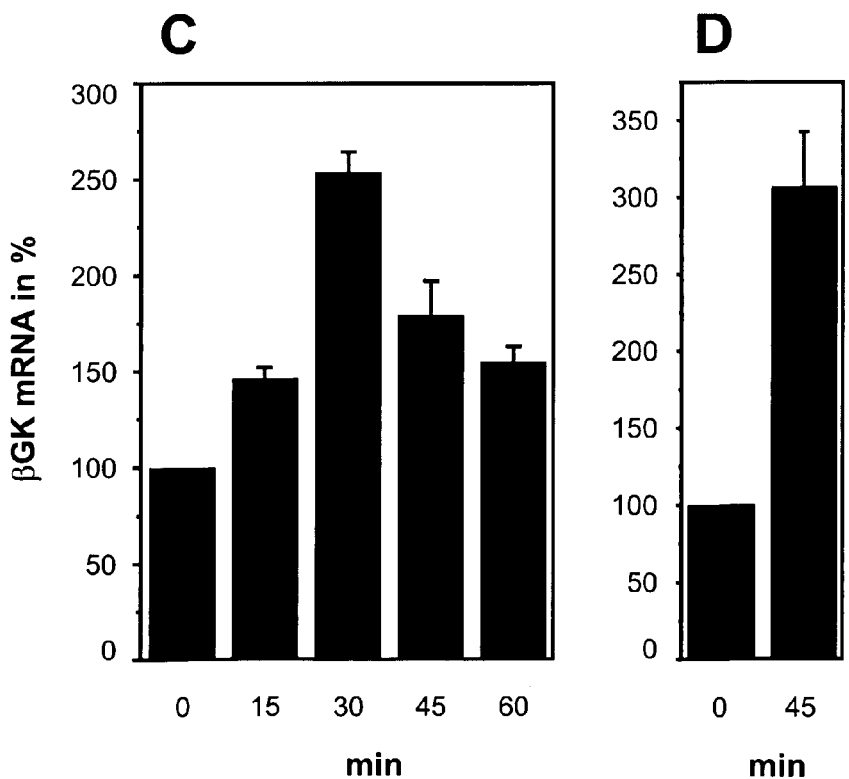

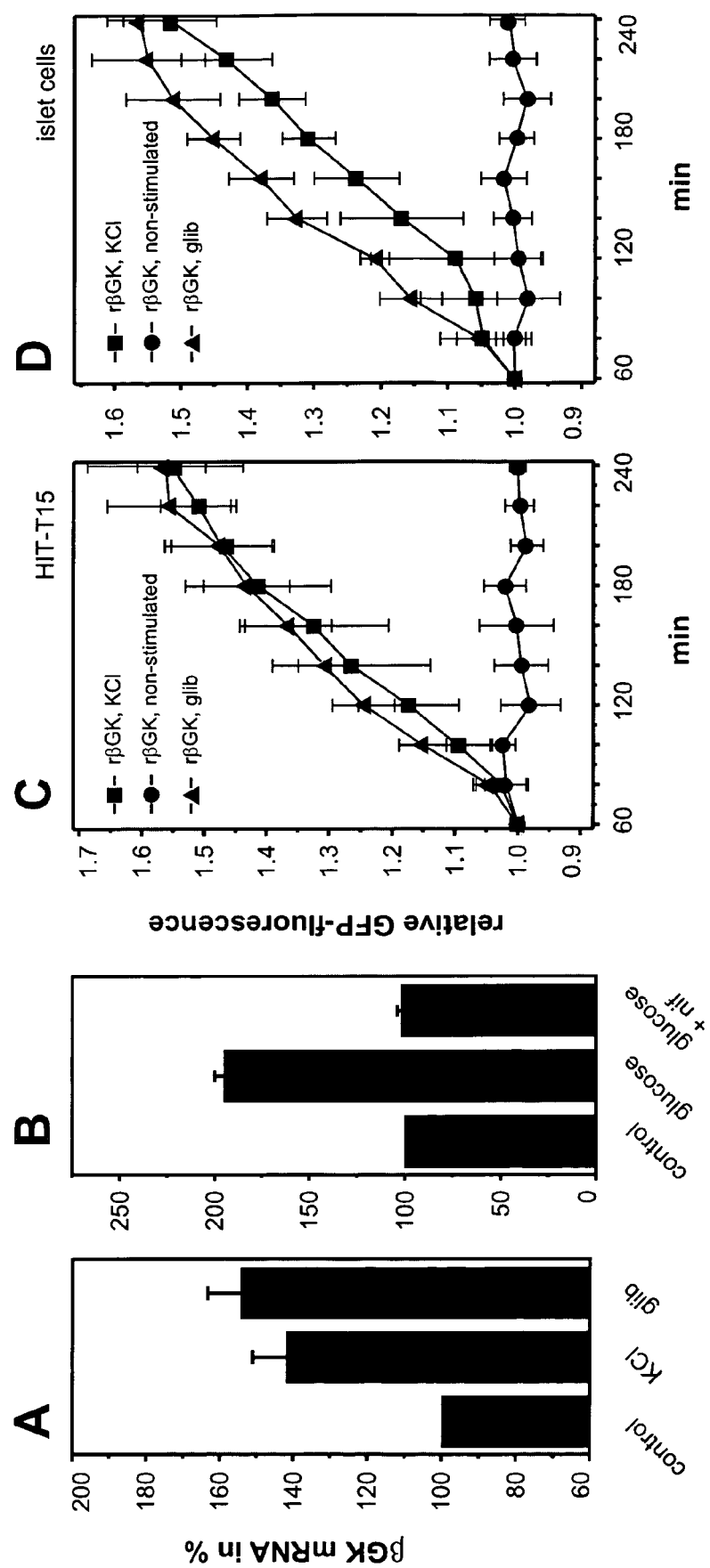
FIGURE 3A-D

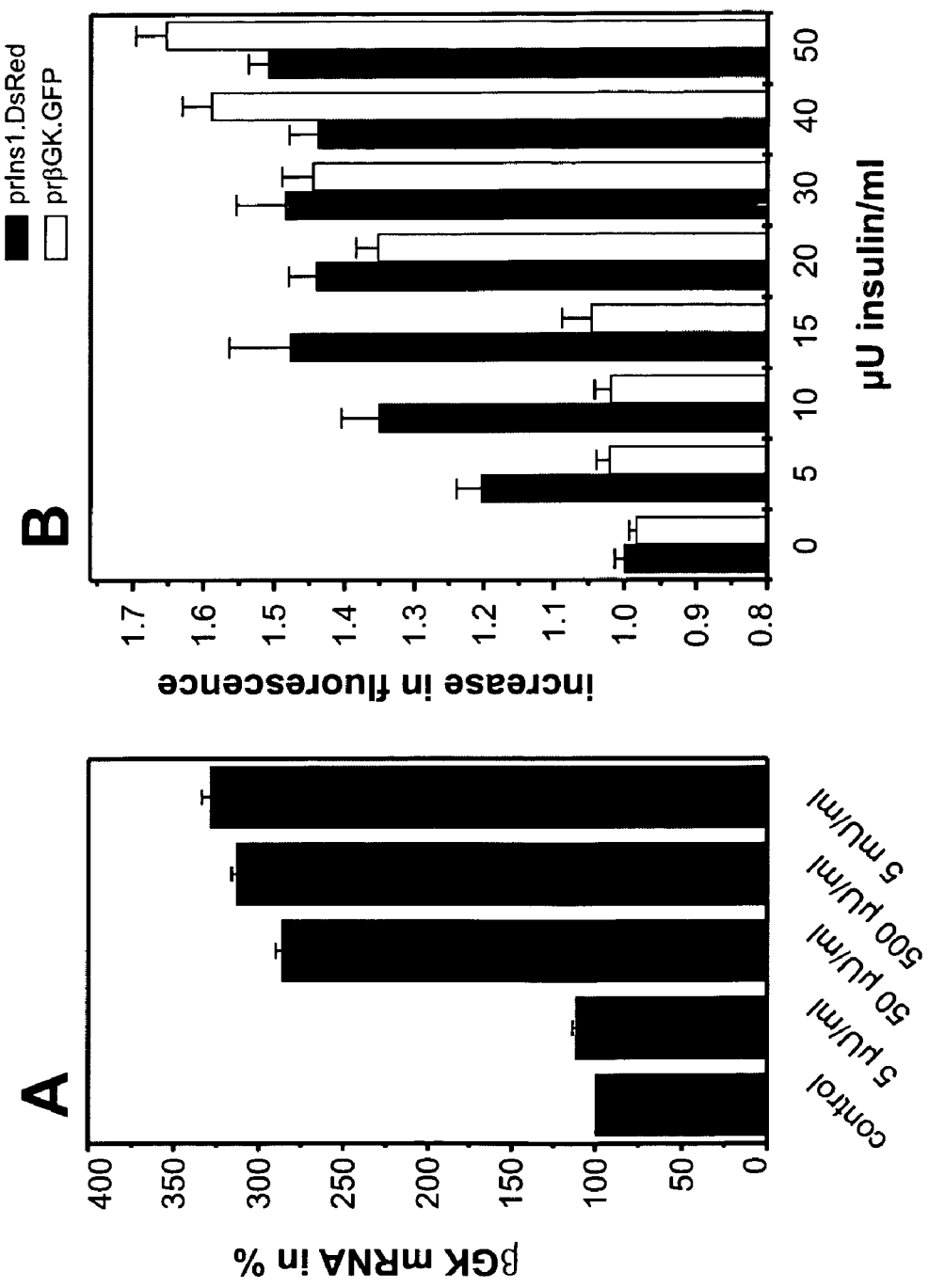
FIGURE 4A-B

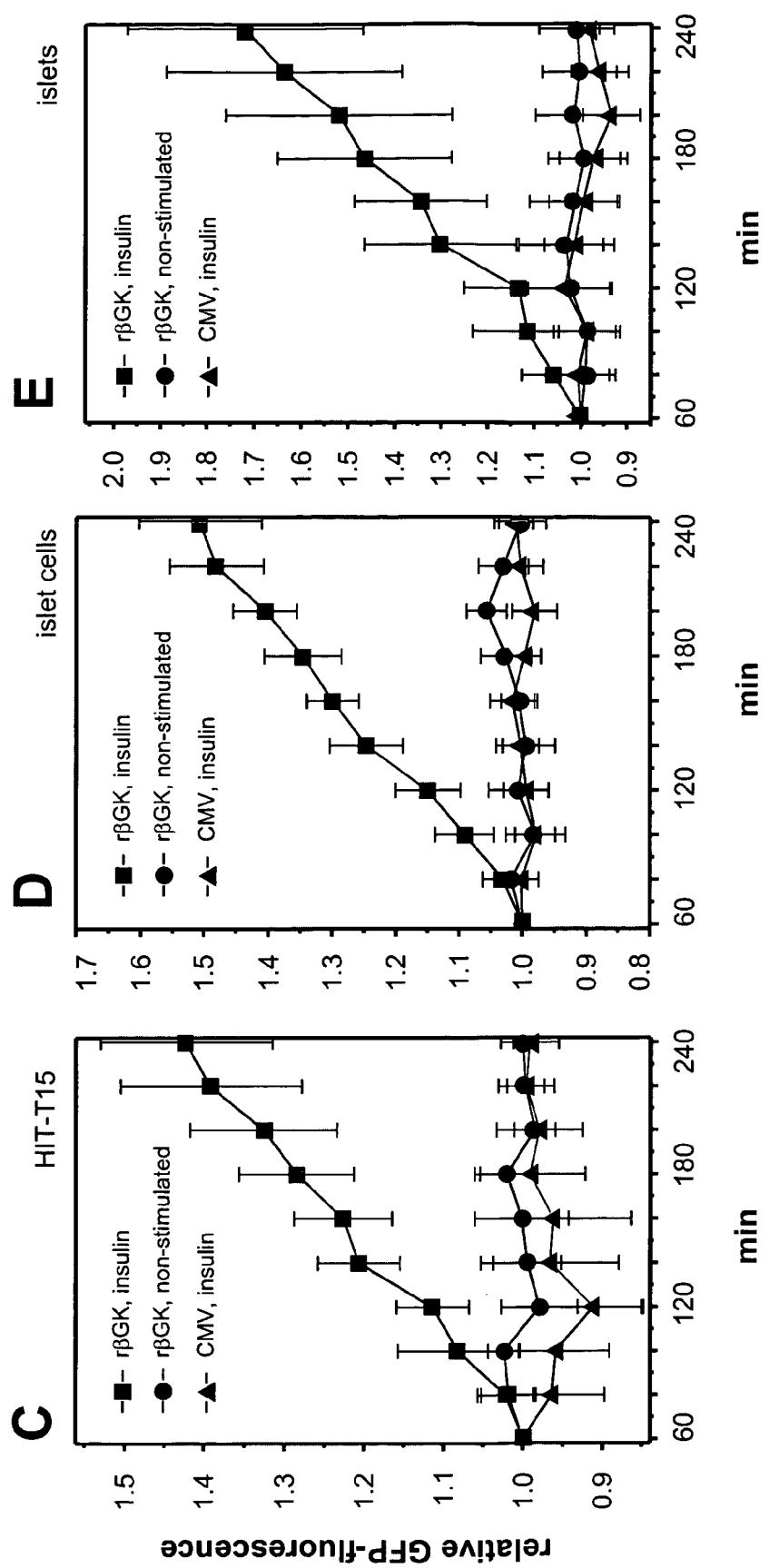
FIGURE 4C-E

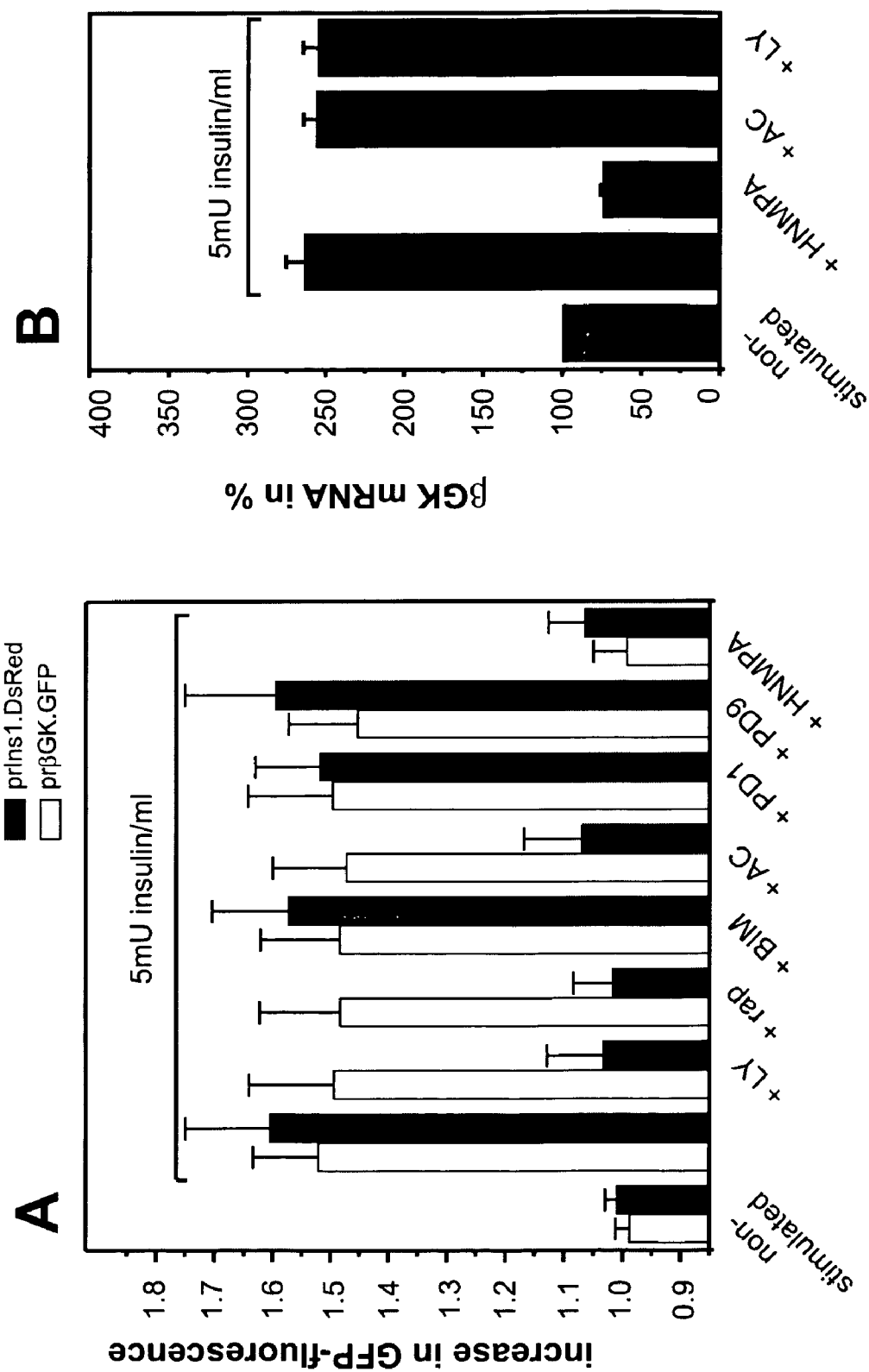
FIGURE 5A-B

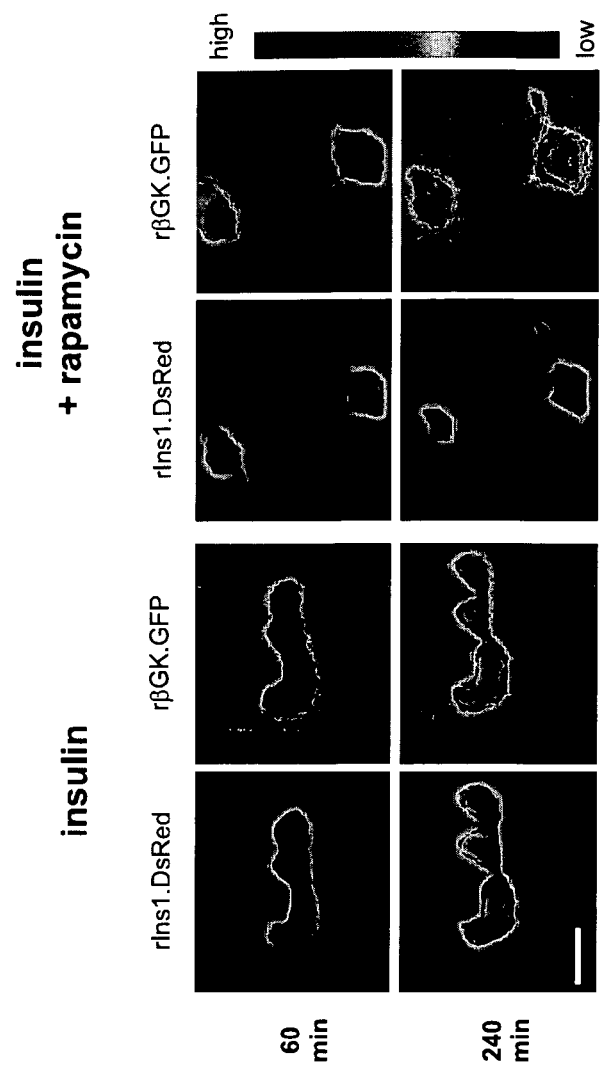
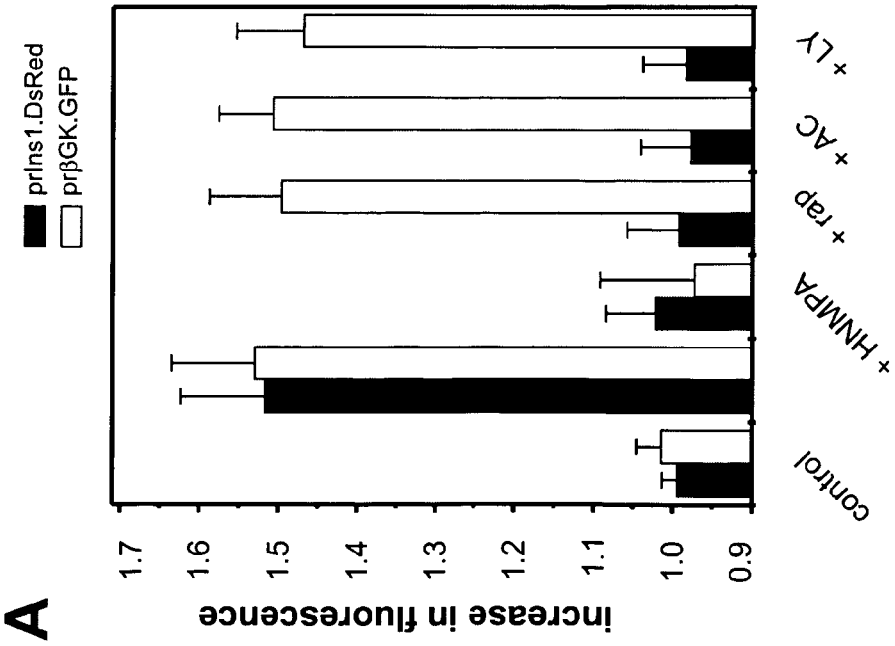
FIGURE 6A-B

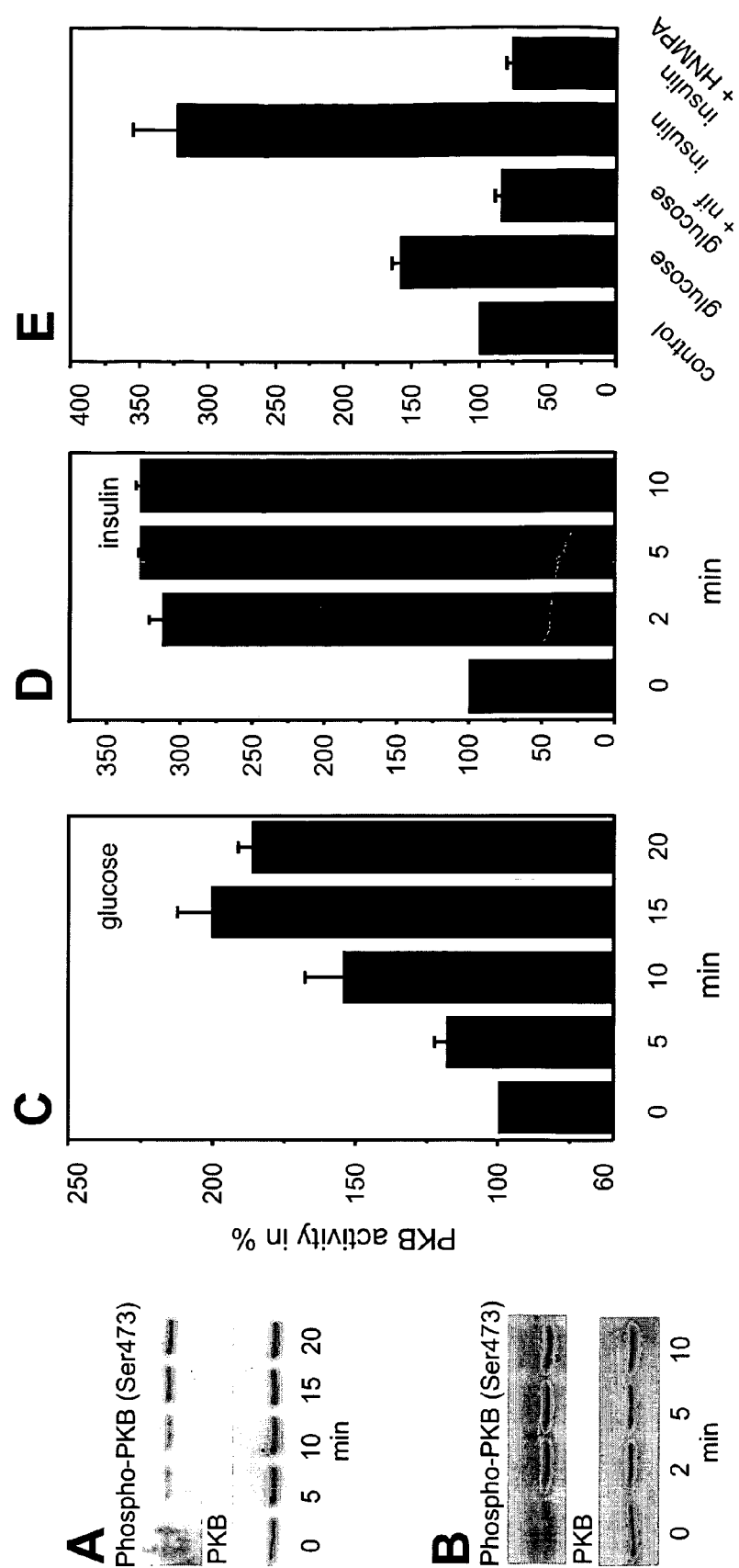
FIGURE 7A-E

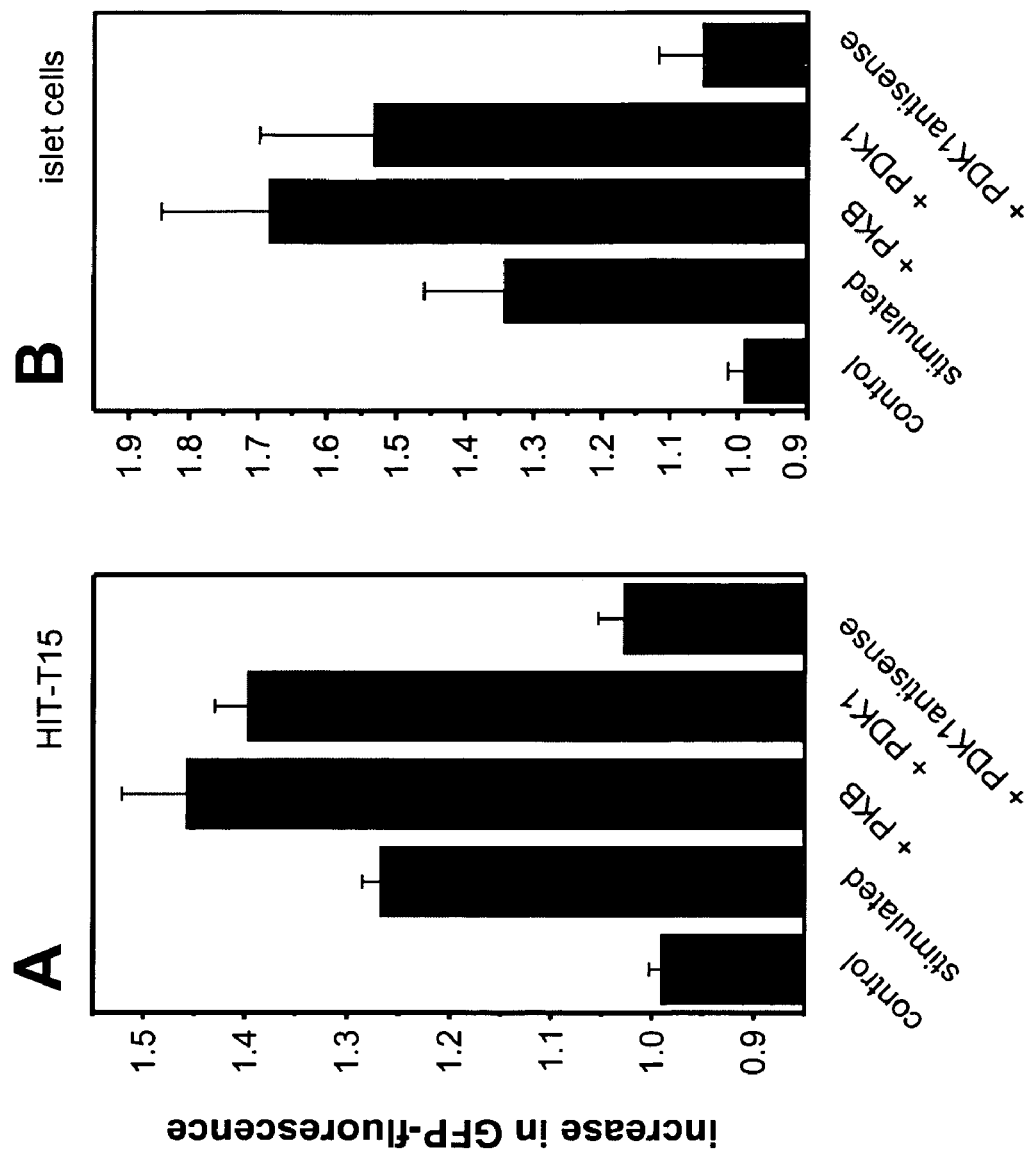
FIGURE 8A-B

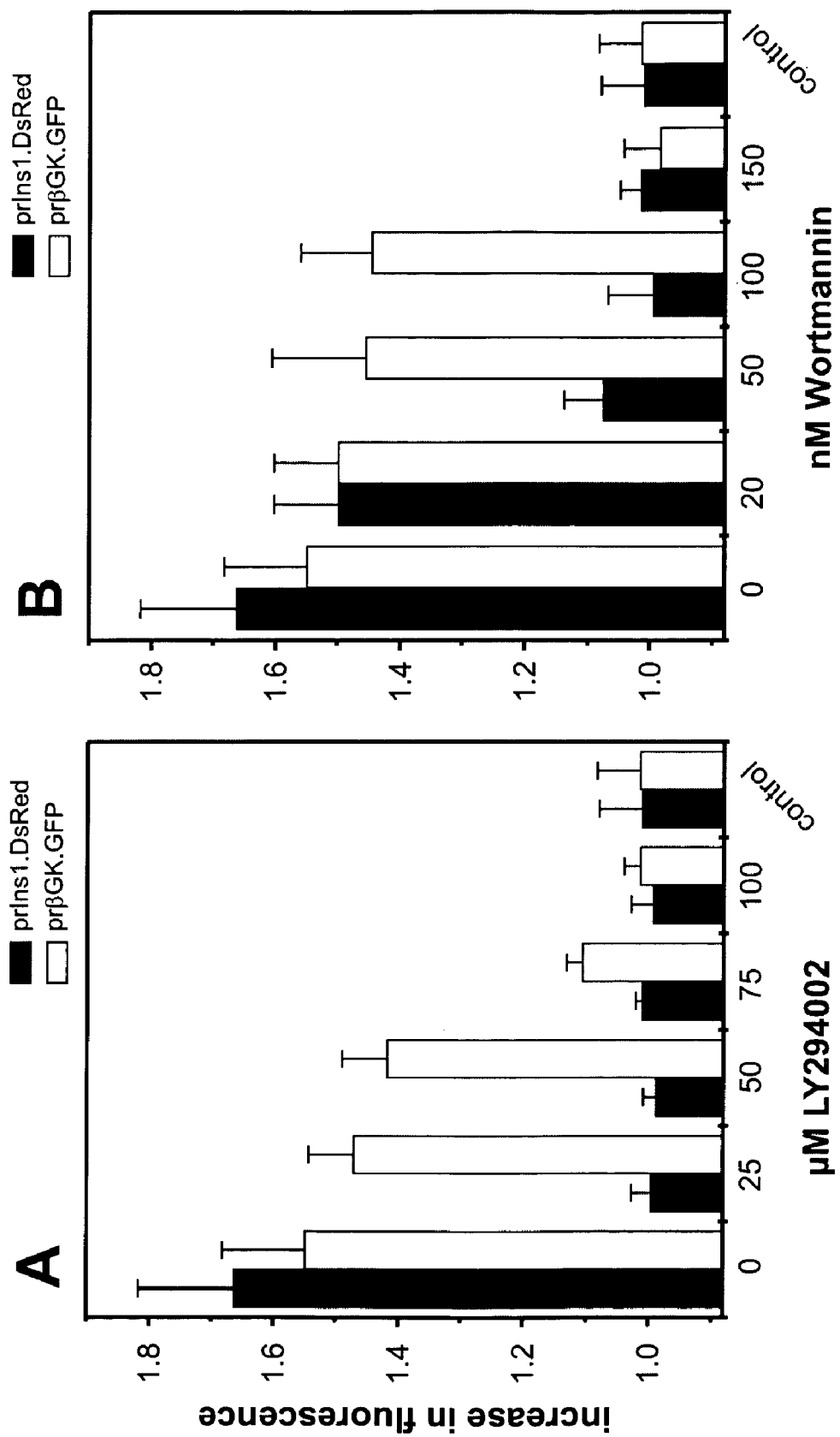
FIGURE 9A-B

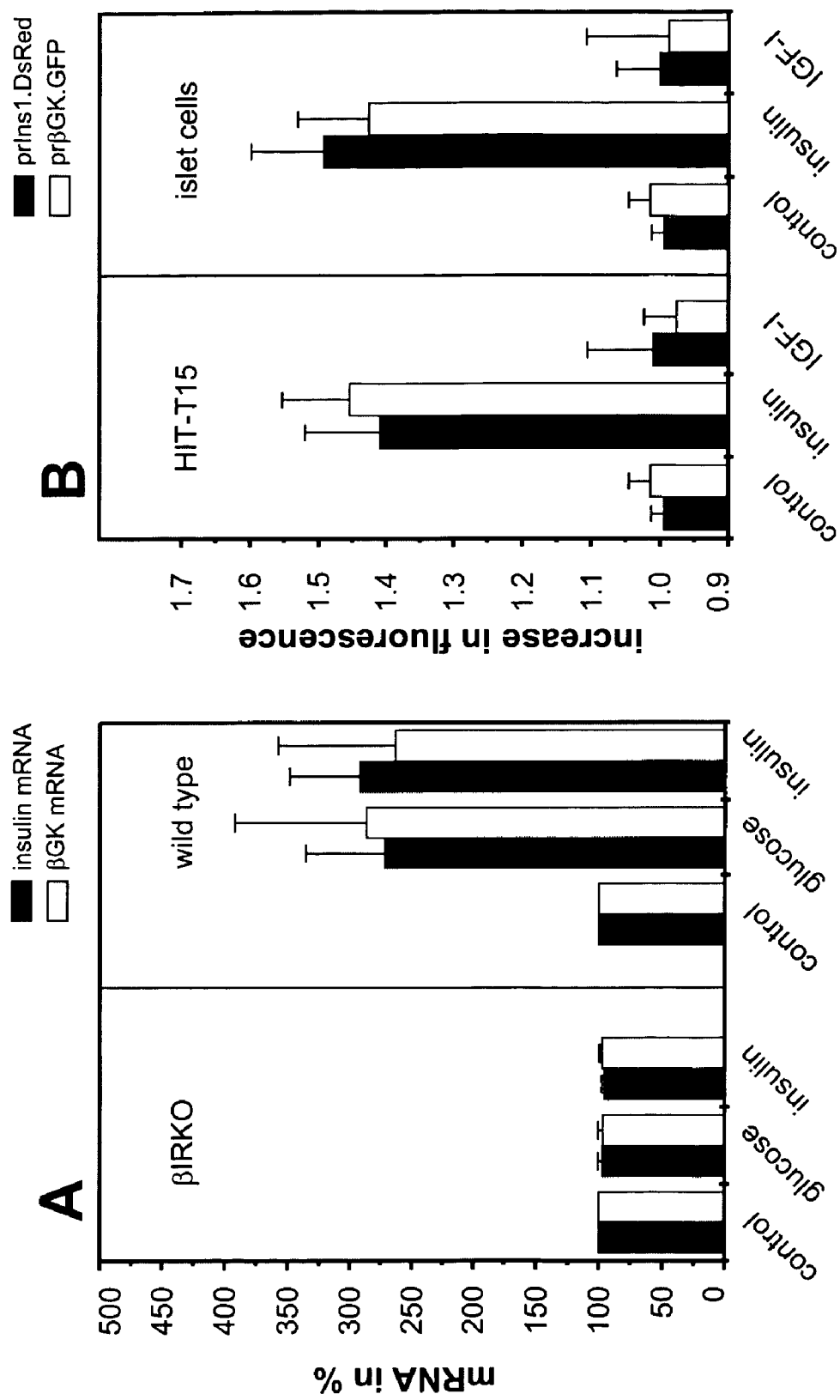
FIGURE 10A-B

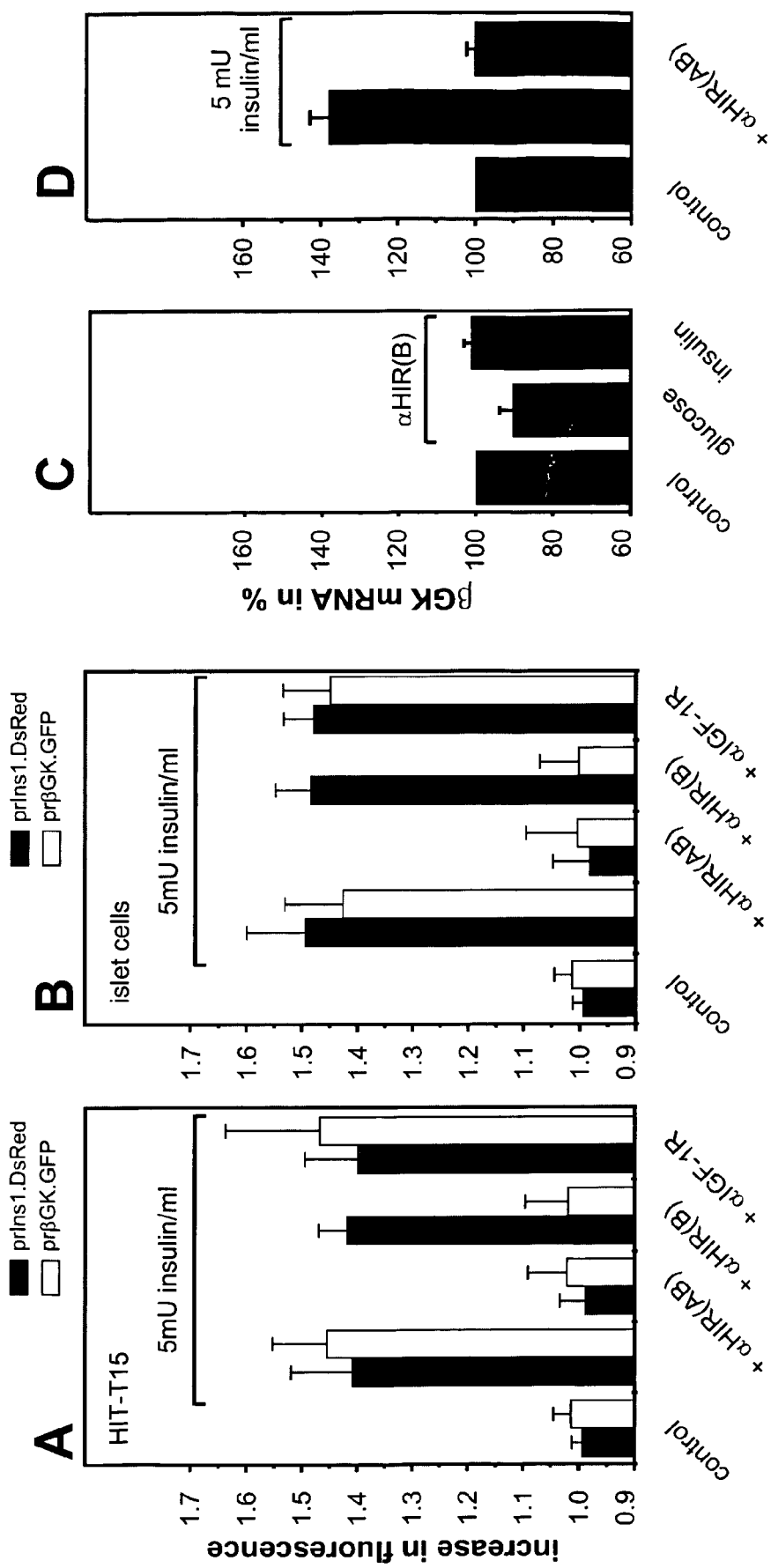
FIGURE 11A-D

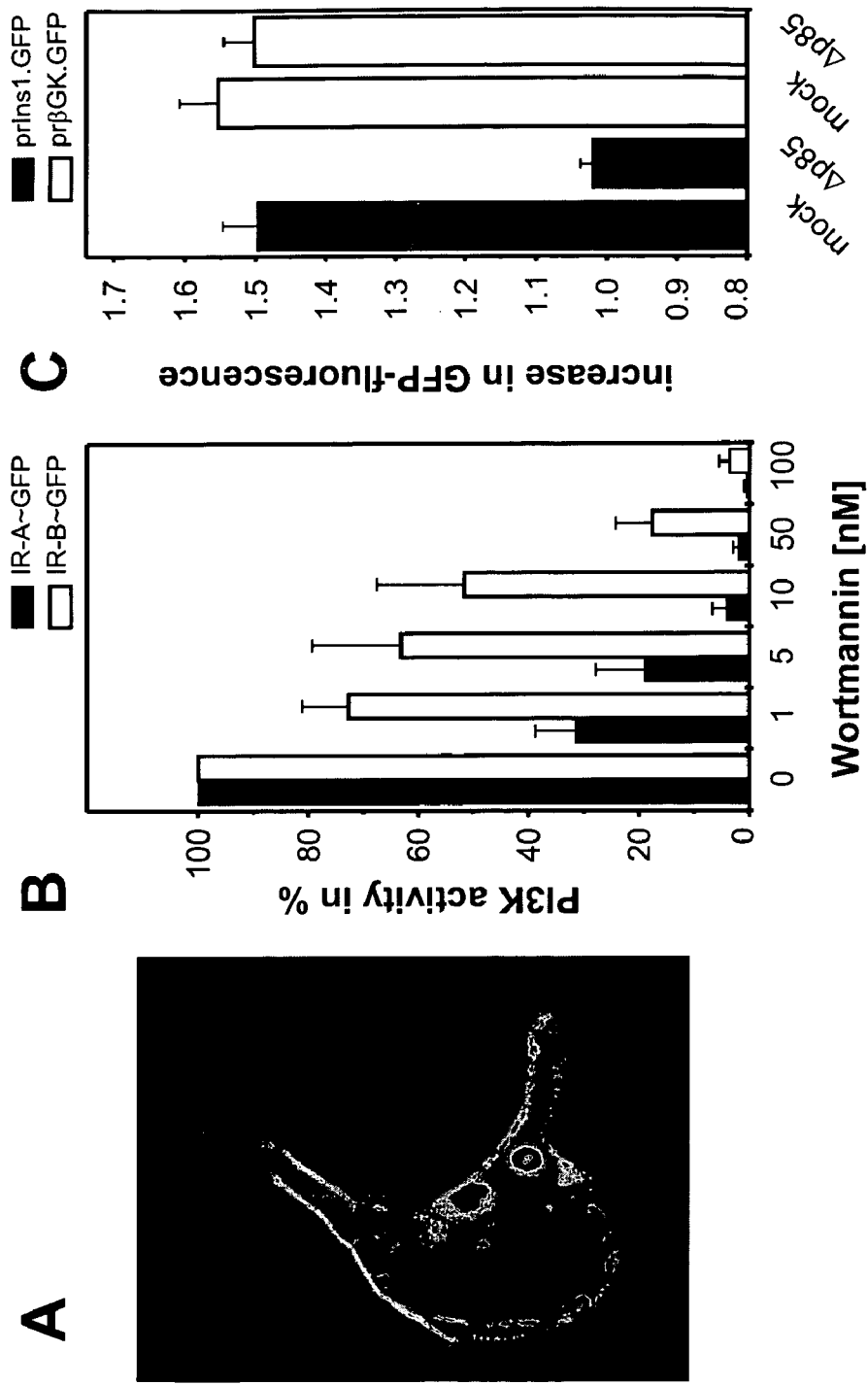
FIGURE 12A-C

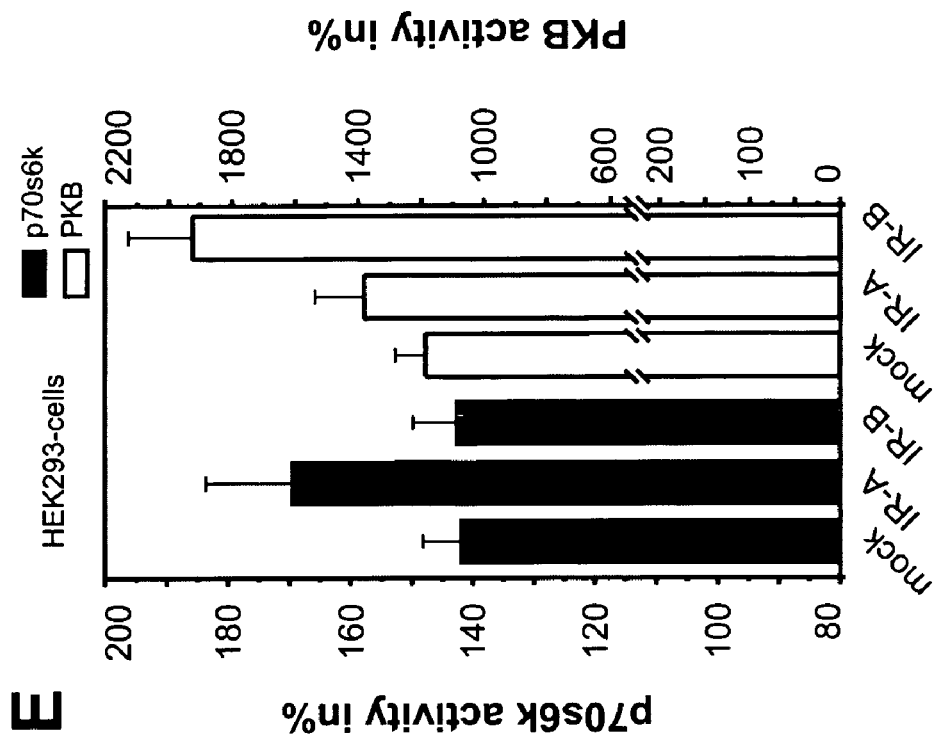
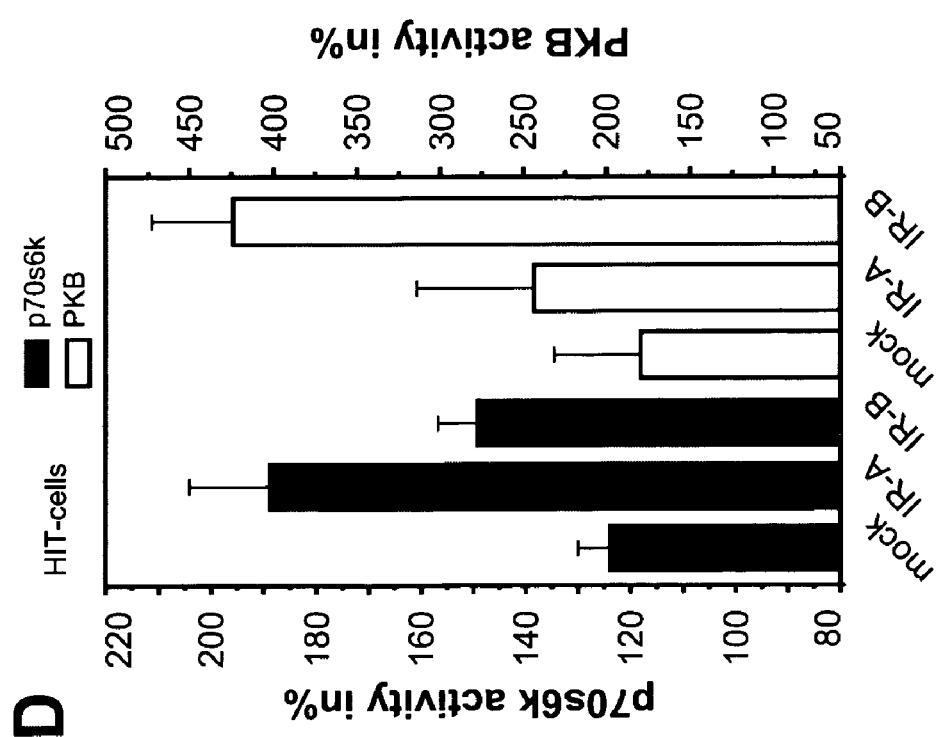
FIGURE 12D-E

MECHANISM FOR IDENTIFYING DRUGS FOR THE TREATMENT OF TYPE II DIABETES

BACKGROUND OF THE INVENTION

Understanding selectivity in signal transduction is one of the most challenging tasks in current cell biology. Over the years, insulin signaling has served as one of the model examples in hormone-induced signal transduction. Complete loss of either insulin or Insulin Receptors (IRs) is lethal. Malfunction of insulin signaling, referred to as insulin resistance, is one of the major causes of type II diabetes (type 2 diabetes mellitus, non-insulin-dependent diabetes mellitus, NIDDM), the most common metabolic disorder in man. Insulin has been shown to exhibit pleiotropic effects, involving mitogenic and/or metabolic events. Moreover, the effect of insulin is tissue- as well as development-dependent. The fact that insulin may transduce its signal through a variety of pathways has been discussed in extensive detail (White and Kahn, 1994). The three major pathways described to date, which employ Insulin Receptors (IRs) as the primary target, include signaling via mitogen activated protein (MAP) kinases, phosphoinositol-3 kinase (PI3K) and phospholipase C. The Insulin Receptor, the first step in these cascades, as a result of alternative mRNA splicing of the $11^{th}$ exon of the (prepro)Insulin Receptor transcript, exists in two isoforms. The A type, or Ex11− (Ullrich et al., 1985), lacks, whereas the B type, or Ex11+ (Ebina et al., 1985), contains the respective sequence coding for 12 amino acids in the C-terminus of the α-chain of the receptor. To date, no insulin-induced effect has been reported that discriminates signaling via A and B type receptors. In fact, the functional significance of these Insulin Receptor (IR) isoforms remains unclear (for a review see Flier et al 1996). Recent studies have shown that also the insulin-producing pancreatic beta cell is a target for insulin action, with insulin effects on transcription, translation, ion flux and exocytosis of insulin (Leibiger et al., 1998a; Kulkarni et al., 1999; Leibiger et al., 2000). In an animal model with a beta cell-specific knockout for Insulin Receptors, a decrease in glucose stimulated insulin release has been shown and a decrease in the insulin content of the cell (Kulkarni et al., 1999). In addition, disruption of insulin signaling in the beta cell at the level of Insulin Receptor substrate-1 or Insulin Receptor substrate-2 leads to altered growth and function of the beta cell. Consequently, insulin resistance, one of the major causes of type II diabetes may not only affect the function of the 'classical' insulin target tissues; muscle, fat and liver, but also apply to the pancreatic beta cell and therefore may affect beta cell function.

SUMMARY OF THE INVENTION

In the present application, for the first time, selective Insulin signaling via the two isoforms of the Insulin Receptor (IR), i.e. IR-A and IR-B type, is shown in a pancreatic beta cell. It is demonstrated that insulin secreted by pancreatic beta cells, upon glucose stimulation, up-regulates insulin gene transcription in an autocrine feedback loop. This autoregulation is mediated by insulin signaling via the A type Insulin Receptor, involving phosphoinositol-3 kinase class Ia, p70s6 kinase and $Ca^{2+}$/calmodulin dependent kinases. Stimulation with either glucose or insulin also leads to an up-regulated expression of the beta-cell transcription unit of the glucokinase gene (βGK). However, in contrast to insulin-stimulated insulin gene transcription, the effect of insulin on beta cell glucokinase gene transcription occurs via the type B Insulin Receptor and protein kinase B (PKB/c-Akt) involving class II-like phosphoinositol-3 kinase. The results described in the present application provide evidence that signaling via either A or B type Insulin Receptors represents a mechanism for selective insulin action.

The surprising findings described herein provide the basic for a first IR-isoform-specific readout system. Thus, the pancreatic beta cell can henceforth serve as a screening tool for drugs and insulin mimetics, wherein IR-A-specific signaling leads to insulin promoter activation and IR-B-specific signaling up-regulates the βGK promoter. In a screening system, measurement of either insulin- and βGK-mRNA levels or insulin- and βGK promoter-driven reporter gene expression can be employed as the actual readout tool. The IR-isoform-specific readout system comprised in the invention can further be used as a screening tool that will allow the development of compounds such as drugs and/or insulin mimetics, that selectively activate either IR-A or IR-B-specific signaling cascades, e.g. in the beta cell and in peripheral tissues. The pronounced expression of IR-B in the classical insulin target tissues implies the importance of the IR-B signaling cascade in these tissues. Consequently, the development of compounds that selectively stimulate the IR-B signaling cascade will improve the function of the beta cell (glucose responsiveness and therefore insulin secretion), as well as the function of the peripheral insulin target tissues (glucose uptake and utilization, protein synthesis, lipid synthesis) and thus potentially provide a treatment that covers the two major causes of non-insulin-dependent diabetes mellitus (NIDDM, type II diabetes), i.e. peripheral insulin resistance and beta cell dysfunction.

DETAILED DISCLOSURE OF THE INVENTION

Insulin signaling is mediated by a complex network of diverging and converging pathways, with alternative proteins and isoforms at almost every step in the process. In the present invention, it is shown that insulin activates the transcription of its own gene and that of the β cell glucokinase gene (βGK) by different mechanisms. Whereas insulin gene transcription is promoted by signaling through Insulin Receptor A type (Ex11−), PI3K class Ia and p70s6k, insulin stimulates the βGK gene by signaling via Insulin Receptor B type (Ex11+), PI3K class II-like activity and PKB (c-Akt). The data provided herein is the first evidence for selectivity in insulin action via the two isoforms of the Insulin Receptor, the molecular basis being preferential signaling through different PI3K and protein kinases.

The molecular mechanisms underlying the selectivity of the cellular effects triggered by insulin are currently discussed as the result of the activation of specific signal transduction pathways. Thus, selectivity may in part be achieved by recruiting and/or activating specific adapter proteins, i.e. Insulin Receptor substrate (IRS) and Shc proteins, that 'channel' the insulin signal in a more defined way by specifically interacting with downstream located effector proteins. Whereas the importance of the various IRS proteins in achieving/maintaining insulin effects in different tissues is currently under extensive investigation (reviewed in Taylor, 1999), the possibility of selective insulin signaling via the two isoforms of the Insulin Receptor has been neglected. This is surprising, because differences in tissue-specific expression as well as in the activation profile of the two receptor isoforms have been described and discussed as a potential mechanism in insulin-specific signaling (as reviewed in Flier et al, 1996). However, no receptor isoform-specific insulin effect has been described so far, which could serve as an 'isoform-specific read-out' to study selective signaling via A and B type Insulin Receptors.

Figure 13:
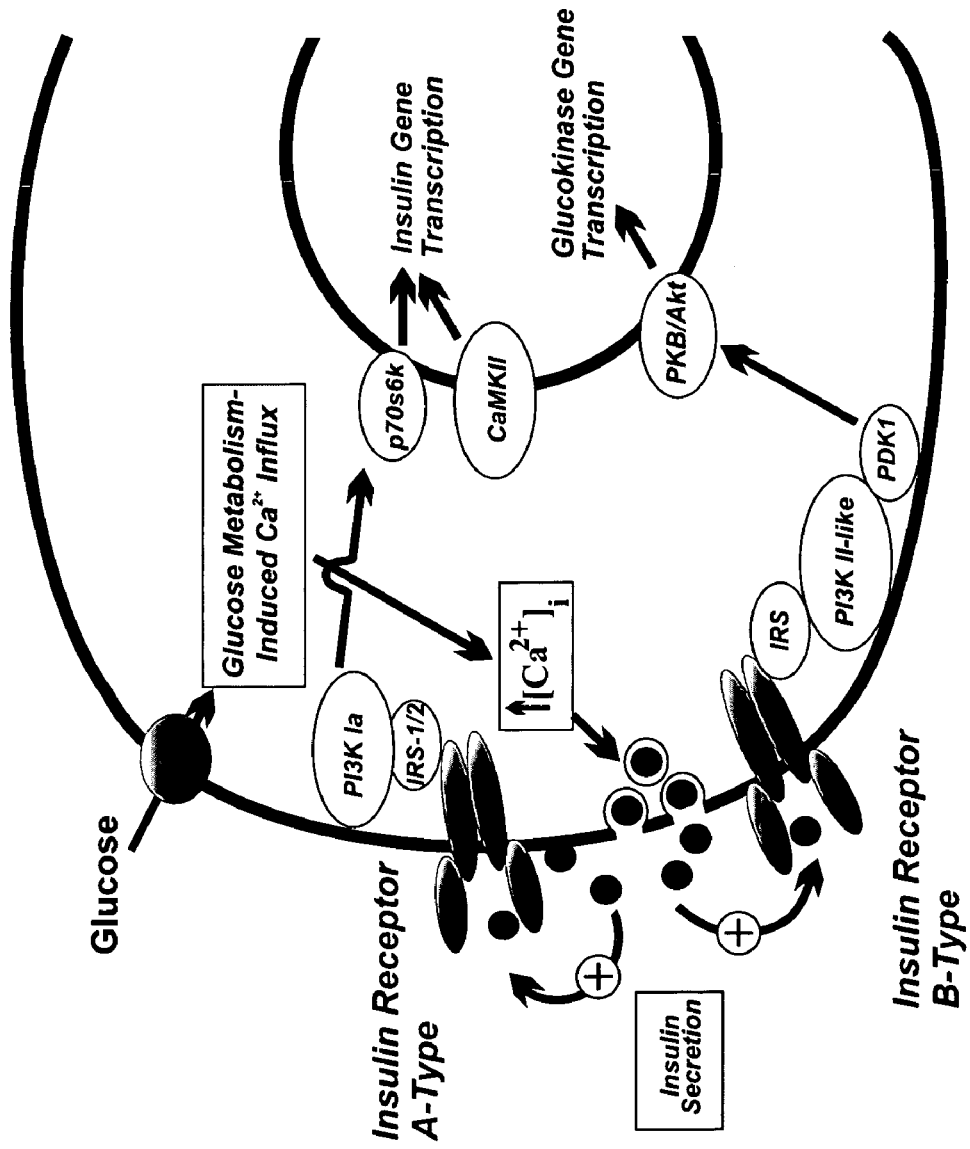

The present invention for the first time provides a 'read-out' system for discriminating selective signaling via the two Insulin Receptor isoforms. It is herein shown that in the pancreatic beta cell glucose/insulin-stimulated transcription of the insulin gene is activated via the Insulin Receptor A type (Ex11-)/PI3K class Ia/p70s6k, while glucose/insulin-stimulated transcription of the glucokinase gene is activated via the Insulin Receptor B type (Ex11+)/PI3K class II-like/PKB(c-Akt) (FIG. 13). Thus, the data clearly demonstrates that selectivity of insulin signaling can be achieved by signaling through the two isoforms of the Insulin Receptor, A and B types, thereby activating different downstream signaling cascades.

The present invention thus relates to an Insulin Receptor isoform-specific readout system comprising the measurement of insulin promoter activation as an indication of insulin Receptor isoform A activation and/or the measurement of βGK promoter activation as an indication of Insulin Receptor isoform B activation.

In the present context, the two Insulin Receptor (IR) isoforms are described as isoforms that exist as a result of alternative mRNA splicing of the $11^{th}$ exon of the insulin (prepro) receptor transcript. The A type (IR-A), or Ex11-, lacks the sequence coding for 12 amino acids in the C-terminus of the α-chain of the receptor, whereas the B type (IR-B), or Ex11+, contains the respective sequence coding for 12 amino acids in the C-terminus of the α-chain of the receptor.

The present invention relates to an Insulin Receptor isoform-specific readout system characterised by measuring insulin promoter activation as an indication of Insulin Receptor A isoform activation as well as measuring βGK promoter activation as an indication of Insulin Receptor isoform B activation.

In a preferred embodiment, an Insulin Receptor isoform-specific readout system is provided, wherein measurement of promoter activation is performed by measuring a reporter gene expression that is controlled by the insulin or βGK promoter, respectively. Measuring promoter activity is herein defined as measuring a change in gene expression of at least one reporter gene or a post-translational modification of an already expressed reporter gene product, the change in gene expression is understood as a change in the level of gene expression, or post-transcriptional modification of the RNA products, post-translational modifications are understood as changes in both the primary structure of the polypeptide and any other modification of the protein, the following examples which are meant to be illustrative and not limiting are phosphorylation, ADP-ribosylation and glycosylation. The change in gene expression related to in the present invention is a variable parameter and will thus differ depending on the expression of which reporter gene is measured, which test substance is tested and which transfected cell system is used.

The measured change in expression level ranges between about 1 fold to 500 fold, such as 1 fold, if no change in expression level is detected, to between 0,01-1 fold, 0,05-1 fold, 0,1-1 fold, 1-10 fold, 1-50 fold, 1-100 fold, 50-200 fold, 50-250 fold, 100-200 fold, 100-300 fold, 100-500 fold, 200-500 fold, 300-500 fold, 400-500 fold, or more, such as at least 10 fold, 20 fold, 50 fold, 100 fold, 200 fold, 300 fold, 400 fold, 500 fold, 600 fold, 700 fold, 800 fold, 900 fold or at least 1000 fold, when change is detected.

The value of the measured change is thus a sensible indicator for the individual potential of each and every test substance and does thereby enable a direct comparisson of the effect of one substance with another. As described in the examples, in one preferred embodiment of the present invention, measuring of reporter gene expression levels is performed by measuring generated fluoresense. In this specific embodiment, the measured change in expression level is typically lower than described above and a significant increase will be in a range of between approximately 1,05-10 fold, or 1,1-5 fold, or 1,05-2,5 fold, such as at least 1,05 fold, 1,1 fold, 1,2 fold, 1,3 fold, 1,4 fold, 1,5 fold, 1,6 fold, 1,7 fold, 1,8 fold, 1,9 fold, 2 fold, 2,1 fold, 2,2 fold, 2,3 fold, 2,4 fold, 2,5 fold, 2,6 fold, 2,7 fold, 2,8 fold, 2,9 fold, 3 fold, 3,1 fold, 3,2 fold, 3,3 fold, 3,4 fold, 3,5 fold, 3,6 fold, 3,7 fold, 3,8 fold, 3,9 fold, 4 fold, 4,1 fold, 4,2 fold, 4,3 fold, 4,4 fold, 4,5 fold, 4,6 fold, 4,7 fold, 4,8 fold, 4,9 fold, 5 fold, or at least 5-10 fold.

In the present invention, measurement of reporter gene expression is preferably performed by measurement of generated fluoresense, such as by measurement of any fluorescence protein, but can as well be obtained by measuring a chemical reaction product, such as by measuring β-galactosidase activity, neomycin phosphotransferase activity, CAT activity, Luciferase activity, or Biotin, or any other detection method well known to a person skilled in the art.

Green fluorescent protein (GFP) is a spontaneously fluorescent protein from the jellyfish, Aequorea victoria. DsRed is a newly cloned red fluorescent protein from Dictosoma sp. The cDNA encoding GFP and/or DsRed can be fused with coding sequences from a number of other proteins; such fusion proteins usually fluoresce as well as retain the biochemical function and cellular localization of the additional protein. A very important aspect of using recombinant, fluorescent proteins in studying cellular functions is the non-invasive nature of the assay. This allows detection of cellular events in intact, living cells.

BFP (Blue), CFP (Cyan) and YFP (Yellow) are color variants of GFP, EGFP is an enhanced variant of GFP. Green fluorescent protein (GFP) and DsRed are widely used as reporters in determining gene expression and protein localization. Different equally preferred embodiments of the present invention provide fusion proteins of any variant of GFP or DsRed with the promoter region of either insulin or βGK, or a combination of both, respectively.

In addition, the vector relating to the present invention is preferably an expression vector in which the DNA sequence encoding the fluorescent protein of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes.

The recombinant vector may further comprise a DNA sequence enabling the vector to replicate in the host cell in question. An example of such a sequence, which is only meant to be illustrative and by no means exclusive, (when the host cell is a mammalian cell) is the SV40 origin of replication. The vector may also comprise a selectable marker, e.g. a gene the product of which complements a defect in the host cell, such as the gene coding for dihydrofolate reductase (DHFR) or the Schizosaccharomyces pombe TPI gene (described by P. R. Russell, 1985), or one which confers resistance to a drug, e.g. ampicillin, kanamycin, tetracyclin, chloramphenicol, neomycin or hygromycin.

The procedures used to ligate the DNA sequences coding for the fluorescent protein of the invention, the promoter and optionally the terminator and/or secretory signal sequence, respectively, and to insert them into suitable vectors containing the information necessary for replication, are well known to persons skilled in the art (cf., for instance, Sambrook et al., 1989).

In an especially preferred embodiment of the invention, an Insulin Receptor isoform-specific readout system is provided, wherein the measurement of βGK promoter activation is performed by measurement of GFP fluorescense. In yet another equally preferred embodiment of the invention, an Insulin Receptor isoform-specific readout system is provided, wherein the measurement of insulin promoter activation is performed by measurement of DsRed fluorescence.

The name "plasmid" refers to an extrachromosomal (usually) self-replicating genetic element. Plasmids are commonly designated by a lower case "p" followed by letters or numbers. The plasmids used herein are either commercially available, publicly available on an unrestricted basis or can be constructed from available plasmids following published procedures. Especially preferred embodiments are the plasmids described in the experimental section, selected from the group consisting of prIns1.DsRed and prβGK.GFP, which are deposited at the DSMZ German Collection of Microorganisms and Cell Cultures, Maschenroder Weg 1b, D-38124 Braunschweig, F.R.G., under the "Budapest Treaty" on the Recognition of the Deposit of Microorganisms for the Purpose of Patent Procedure. The deposit number for prIns1.DsRed is DMS 14212 and the deposit number for prβGK.GFP is DSM 14213. In addition, equivalent plasmids to those described are known and are apparent to the skilled worker in this field.

The term "vector" stands for a nuclelc acid compound used for the transformation of cells. A vector contains polynucleotide sequences corresponding to appropriate protein molecules, which when combined with appropriate control sequences confer specific properties on the host cell to be transformed. Plasmids, viruses and bacteriophage are suitable vectors. Artificial vectors can be constructed by cutting and joining DNA molecules from different sources using restriction enzymes and ligases. The term vector also includes recombinant DNA cloning vectors and recombinant DNA expression vectors. In addition to the plasmids mentioned above, also some viruses can be appropriate vectors. For example the adenovirus, the adeno-associated virus, the vaccinia virus, the herpes virus, the Rous sarcoma virus and the baculovirus are useful. The baculovirus based expression system taken as an example is an eukaryotic expression system and thus uses many of the protein modification, processing and transport systems present in higher eukaryotic cells. The baculovirus expression system uses a helper-independent virus, which can be propagated to high titers in insect cells adapted for growth in suspension cultures, making it easy to obtain large amounts of recombinant protein. Several alternate methods of expression are described in J. Sambrook et al, 1989, at 16.3-17.44.

"Recombinant DNA cloning vector" refers to any autonomously replicating agent, also including plasmids and phages comprising a DNA molecule to which one or more additional DNA segments can or have been added.

"Recombinant DNA expression vector" refers to any recombinant DNA cloning vector in which a promoter has been incorporated, to control the transcription of the inserted DNA. "Promoter" stands for a DNA sequence, which directs transcription of DNA to RNA. The term "expression vector system" refers to a recombinant DNA expression vector in combination with one or more transacting factors that specifically influence transcription, stability or replication of the recombinant DNA expression vector. The trans-acting factor can be expressed from a co-transfected plasmid, virus or other extrachromosomal element. It also may be expressed from a gene integrated within the chromosome. The name "transcription" refers to the process of transferring information from a DNA sequence to a complementary RNA strand.

"Translation" refers to the process in which the genetic information of messenger RNA is used to specify and direct the synthesis of a polypeptide chain.

Little, if anything, is known about selective insulin signaling via A and B type insulin Receptors in the prior art. Data on tissue-specific expression of the two isoforms, measured as level of mRNA in a very restricted set of tissues, revealed a predominant expression of IR-B in liver and muscle while the IR-A was mainly expressed in spleen and brain. Attempts to correlate tissue-specific expression of the receptor isoforms with type II diabetes has generated conflicting results that do not clarify the functional role of either isoform. Studies of the activation profiles of the two receptor isoforms by insulin showed a higher affinity for insulin (2-fold) for IR-A. Besides the affinity for insulin, differences in their kinase activity, as well as internalization and recycling have been described. These data imply differences in the function of either IR isoform, but no isoform-specific insulin-induced effect has been reported, so far. In fact, the functional significance of these IR isoforms has remained unclear.

Recent studies from several laboratories have shown that beside the classical insulin targets liver, muscle and fat, also the insulin-producing pancreatic beta cell is a target for positive insulin action with insulin effects on transcription, translation, $Ca^{2+}$ flux and exocytosis and potential importance for beta cell survival and/or proliferation.

Studying insulin—dependent transcription of the insulin—and the glucokinase (βGK) genes in the beta cell, the inventors found that both genes are regulated by insulin, utilizing different mechanisms in signal transduction. Whereas insulin activates the transcription of its own gene by signaling via the IR-A/PI3K class Ia/p70s6k, insulin up-regulates βGK transcription by signaling via IR-B/PI3K class II-like/PKB(c-Akt).

The inventors demonstrate that the molecular basis for the IR isoform selectivity is provided by the different localization of the two IR isoforms in the plasma membrane and their different sensitivity for insulin. Mechanistically, this enables preferential activation of IR-A/PI3K Ia/p70s6k in pancreatic β cell glucose/insulin-stimulated insulin gene transcription and IR-B/PI3K class II-like/PKB in glucose/insulin-stimulated βGK transcription (as schematised in FIG. 13). That this specificity in signaling has a wider implication than to the pancreatic β cell is demonstrated by the data obtained in non-insulin producing HEK293 cells. The fact that the selectivity of insulin signaling is gained by signaling through the two IR isoforms reinforces the concept of the pancreatic β cell as a target for positive insulin action.

The present invention thus provides a first IR-isoform-specific readout system. Therefore, the pancreatic beta cell can serve as a screening tool for drugs and insulin mimetics where IR-A-specific signalling leads to insulin promoter activation and IR-B-specific signalling up-regulates the βGK promoter. In a screening system, measurement of either insulin-mRNA levels and βGK-mRNA levels or insulin- and βGK-promoter-driven reporter gene expression will serve as a readout.

In a preferred embodiment of the present invention, a suitable cell is therfore transfected with at least one plasmid selected from the group consisting of prIns1.DsRed and prβ-GK.GFP, as described in the experimental section in detail.

In the present context, "transformation" means the introduction of DNA into an organism in a way that it can replicate itself, either as an extrachromosomal element or by chromosomal integration. Methods of transforming bacterial and eukaryotic hosts are well known. Transformation of the mammalian cells can be performed by any of the known processes including, but not limited to, the protoplast fusion method, the calcium phosphate co-precipitation method, electroporation, liposome-mediated transfection and more, described for example in Current Protocols in molecular biology, Wiley Interscience. Other ways of production are well known to experienced people in the field and are summarised in J. Sambrook, et al., (1989).

"Transfection" is herein used to describe the operation of adding an expression vector to a host cell, whereby the cell itself takes up the DNA molecule into its nucleus and either integrates it into the chromosomes (stable transfection) or keeps it separate from the chromosomal DNA in the nucleus as a transient transcribed plasmid (transient transfection). Many different methods of transfection are known, for example calcium phosphate co-precipitation and electroporation. A successful transfection can be monitored by a specific site introduced in the transfected DNA molecule, which can be recognized by an antibody. This DNA site can either be a specifically introduced "flag" or "tag", meaning a specific sequence, which is easily recognized by an antibody. It could also be an intrinsic part of the expressed gene, recognized by a specific antibody. Another preferred possibility e.g. would be the fusion to a fluorescent protein like GFP (green fluorescent protein).

A suitable cell in the present context comprises a cell in or from a cell culture, or in or from a primary cell culture, or a cell that is isolated from a sample, such as from a pancreas sample, muscle, fat or liver sample. In a preferred embodiment of the present invention, said suitable cell is a mammalian cell, such as a mouse, rat, dog, cat, pig hamster or human cell. In a most preferred embodiment, said suitable cell is further characterised as a pancreatic beta cell, such as a stable or transiently transfected isolated pancreatic islets cells or a insulin-producing HIT-T15 cell. Additional, in the present context suitable and publicly available and broadly used insulin-producing cell lines are MIN6, INS-1, βTC cell lines, RIN cell lines. In a most preferred embodiment of the invention, such cell transiently expresses the gene product of a plasmid, selected from the group consisting of prIns1.DsRed and prβ-GK.GFP.

The transformed or transfected host cell described above is cultured in a suitable nutrient medium under conditions permitting the expression of the present DNA construct after which the cells may be used in the screening method of the invention. Alternatively, the cells may be disrupted after which cell extracts and/or supernatants may be analysed for reporter gene expressed products, such as fluorescence.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). In one method of the invention, the fluorescence of cells transformed or transfected with the DNA construct of the invention may suitably be measured in a spectrometer or a fluorescence microscope, wherein the spectral properties of the cells in liquid culture may be determined as scans of light excitation and emission.

The time needed to generate a detectable amount of product will vary depending on the assay system. A sensitive assay system will require less time to generate a detectable amount of product than a less sensitive assay system. For example, a fluorescent or chemiluminescent assay system will generally require less time to generate a detectable amount of product than a colorimetric assay system. One of skill in the art will know the amount of time sufficient to measure receptor activity based upon the assay system.

In a preferred embodiment of the invention, an insulin producing cell line is created that stably expresses DsRed under the control of the rat insulin-I gene promoter (as a marker for signaling via the A type Insulin Receptor) and that stably expresses GFP under the control of the rat βGK promoter (as a marker for signaling via the B type Insulin Receptor). E.g., insulin producing cells, like HIT-T15, (MIN6, INS1, or similar), are stably transfected with prIns1.DsRed and prβGK.GFP. The following three approaches can be employed to gain said cell line. 1) Cells are transfected with a plasmid that contains the expression cassettes for prIns1.DsRed, prβGK.GFP and a selection marker, providing resistance to a selection marker, such as genicitin. 2) Cells are co-transfected with one plasmid that contains the expression cassettes for prIns1.DsRed and prβGK.GFP and with a second plasmid, that encodes the selection marker. 3) Cells are co-transfected with two plasmids, the first containing the expression cassettes for prIns1.DsRed and selection marker 1 and the second containing expression cassettes for prβ-GK.GFP and selection marker 2 (hygromycin-B resistance for example). Following transfection by the lipofectamine technique, cells are cultured in the presence of the respective selection marker. Clones of cells are raised from single cells and tested and selected for simultaneous GFP and DsRed expression. The candidate-cell clone expresses both GFP and DsRed, does increase GFP and DsRed expression in response to insulin stimulation (e.g. 5 mU/ml at substimulatory glucose concentrations, depending on the cell type used), and allows selective signaling via A and B type Insulin Receptors, as verified by employing B type-receptor-specific blocking antibodies.

The present Invention further provides a method for determining the selectivity of a test substance for Insulin Receptor isoform A versus Insulin Receptor isoform B, comprising measuring the ratio between insulin promoter activation and βGK promoter activation that is induced by providing said test substance. Said method is preferably characterised by transfecting a suitable cultured or isolated cell with at least one genetical element comprising a suitable reporter gene under contol of either an insulin promoter or a βGK promoter, exposing said cell to a test substance in an amount sufficient to influence cellular response, and measuring the selective influence of said test substance on insulin promoter activation and/or βGK promoter activation by measuring the level of reporter gene expression.

An especially preferred Insulin Receptor isoform-specific readout system according to the present invention is characterised by transfecting a suitable cultured or isolated cell with at least one genetical element comprising a suitable reporter gene under contol of either an insulin promoter or a βGK promoter, exposing said cell to a test substance in an amount sufficient to influence receptor activation, and measuring the selective influence of said test substance on insulin promoter activation and/or βGK promoter activation by measuring the level of reporter gene expression.

The term "genetic element" generally means a polynucleotide comprising a region that encodes a polypeptide or a region that regulates transcription or translation and/or other processes important to expression of the polypeptide in a host cell, or a polynucleotide comprising both a region that encodes a polypeptide and a region operably linked thereto that regulates expression.

Genetic elements comprise a polynucleotide molecule that replicates as an episomal element; that is, as a molecule physically independent of the host cell genome. They are decribed above as plasmid, virus, retrovirus, bacteriophage, cosmid, artificial chromosome (bacterial or yeast), or a nucleic acid sequence that behaves as an autonomous unit of polynucleotide replication within a cell.

In one particular embodiment, the present invention encompasses rapid, high-throughput assays for screening one or more test substances. High-throughput screening is a technique well known to the skilled artisan.

The term "test substance" as used herein, refers to a chemically defined compound, agent, or mixture of compounds whose effect on an IR isoform activity is determined in an assay of the present invention. Test substances include, but are not limited to, drugs, ligands (natural or synthetic), ligand antagonists, polypeptides, peptides, peptide mimics, polysaccharides, saccharides, glycoproteins, nucleic acids, DNA and RNA strands oligonucleotides and small organic molecules. In one embodiment, test substances comprise an existing library of compounds or agents. In another embodiment, test substances comprise a novel library of compounds or agents. In another embodiment, test substances used in assays of the present invention are purified, partially purified, or unpurified (i. e., not purified from other components).

Preferred, but not limitted to, are test substances selected from the group consisting of insulin analogs, insulin mimetics, plant or fungal extracts, pharmacological inhibitors of cellular or nuclear receptors, kinase inhibitors, kinase activators, kinases, phosphatases, phosphatase inhibitors, phosphatase activators, or modified peptides.

In a preferred embodiment, the present invention thus provides a method for screening for insulin analoga and insulin mimetics that trigger and/or enhance signaling via insulin Receptors.

In such an embodiment, the candidate-cell clone is cultured in the respective culture medium in 96-well microtiter plates at 37° C. and 5% CO2. Prior to stimulation with insulin analoga or insulin mimetics, cells are incubated at substimulatory glucose concentrations (conditions depending on the cell line used). Screening is performed by applying the individual test substance to a defined well of the microtiter plate, measuring DsRed and GFP fluorescence levels after application of the substance (time point 1). This is e.g. done by using a microtiter plate fluorescence reader, such as Fusion Universal Microplate Analyzer (Packard). Cells are measured for GFP and DsRed fluorescence again at 4 hrs after application of the test substance (time point 2). The comparison of fluorescence 'time point 1' versus fluorescence 'time point 2' thus provides the following characterization of the test substances: 1) no increase in either GFP or DsRed fluorescence: no activation of signaling via either A or B type Insulin Receptor. 2) increase in GFP fluorescence but not in DsRed fluorescence: activation of signaling via B type Insulin Receptor. 3) increase in DsRed fluorescence but not GFP fluorescence: activation of signaling via A type Insulin Receptor. 3) increase in DsRed and GFP fluorescence: activation of signaling through both A and B type Insulin Receptors.

Another equally preferred embodiment of the present invention further provides a method for for screening for substances/compounds that abolish and/or decrease signaling via Insulin Receptors. The candidate-cell clone is cultured in the respective culture medium in 96-well microtiter plates at 37° C. and 5% CO2. Cells are incubated at substimulatory glucose concentrations (conditions depending on the cell line used). Screening is performed by applying the individual test substance to a defined well of the microtiter plate. Following an incubation period (e.g. 30 min), cells are stimulated with 5 mU insulin/ml and DsRed and GFP fluorescence levels are measured (time point 1). Cells are measured for GFP and DsRed fluorescence a second time 4 hrs after insulin stimulation (time point 2). The comparison of fluorescence(time point 1) versus fluorescence (time point 2) provides the following characterization of the test substances: 1) no increase in either GFP or DsRed fluorescence: repression of signaling via both A or B type insulin Receptor. 2) increase in GFP fluorescence but not in DsRed fluorescence: repression of signaling via A type Insulin Receptor. 3) increase in DsRed fluorescence but not GFP fluorescence: repression of signaling via B type Insulin Receptor. 3) ) Increase in DsRed and GFP fluorescence: no repression of signaling via any Insulin Receptors. The IR-isoform-specific readout system of the present invention is a screening tool that will allow the development of compounds, such as drugs and/or insulin mimetics, that selectively activate IR-B-specific signalling cascades in the beta cell and in the peripheral tissues. The pronounced expression of IR-B in the classical insulin target tissues implies the importance of the IR-B signalling cascade in these tissues.

In the beta cell, βGK is thought to be the glucose-sensor. Dysfunction of βGK causes the MODY2 type of type II diabetes. Consequentely, the development of compounds that selectively stimulate the IR-B signalling cascade will improve the function of the beta cell (e.g. in its glucose responsiveness and therefore insulin secretion), as well as the function of the peripheral insulin target tissues (e.g. in their glucose uptake and utilization, protein synthesis and lipid synthesis). Thus, the present invention provides a possible treatment that covers the two major causes of non-insulin-dependent type II diabetes (NIDDM, type II diabetes), i.e. peripheral insulin resistance and beta cell dysfunction.

The substances found via the screening methods described I the present invention are thus not strictly limited to substances that directly bind to or block or have any other direct effect on the respective IR isoforms, but do consequently also encompass substances that generate influence on any other part of the receptor isoform specific signalling cascade in the cell. E.g. such a substance can be activating, enhancing or repressing the signalling pathway at the PI3 class II-like kinase, or protein kinase B (PKB/c-Akt) or at the PI3 class Ia, or p70s6 kinase, respectively.

The present invention therefore ultimately relates to a method of treatment of Type II Diabetes comprising administering a drug selective for Insulin Receptor isoform B to a patient in need thereof, or administering a drug selective for Insulin Receptor isoform A to a patient in need thereof, or administering a drug that acts at a later step in the respective signalling pathways of one of the receptor isoforms. In such a treatment, the signalling cascade of a respective Insulin Receptor isoform is either activated, or the activation of the signalling cascade of said respective Insulin Receptor isoform is inhibited.

A method is provided for identifying a drug capable of stimulating βGK transcription comprising the steps of testing whether it activates or blocks cellular signalling through Insulin Receptor isoform B, and/or PI3 class II-like kinase/protein kinase B (PKB/c-Akt). As well as a method for identifying a drug capable of stimulating or repressing insulin transcription, comprising the steps of testing whether it activates or blocks cellular signalling through Insulin Receptor isoform A, and/or PI3 class Ia/p70s6 kinase Furthermore, the present invention encompasses a method of treatment of Type II Diabetes comprising administering a drug capable of selectively stimulating either βGK transcription or insulin transcription in pancreatic beta cells, to a patient in need thereof.

A pharmaceutical composition is provided comprising a compound, the compound being selective for Insulin Receptor isoform B or for Insulin Receptor isoform A and a market authorisation, the market authorisation being based on an application for market authorisation comprising data showing selectivity for Insulin Receptor isoform B or selectivity for Insulin Receptor isoform B, respectively, for treating Type II diabetes.

For clinical application of a compound selective for a Insulin Receptor isoform, the compound should preferably be prepared as a pharmaceutical composition appropriate for the intended application. Generally, this will entail preparing a pharmaceutical composition that is essentially free of pyrogens, as well as any other impurities that could be harmful to humans or animals. Also, one will generally desire to employ appropriate salts and buffers to render the composition stable and allow for composition-uptake by a target cell and other modifications as will be known to the person skilled in the art.

The phrases "pharmaceutically" or "pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and anti-fungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated.

Supplementary active ingredients can be incorporated into the compositions.

A compound of the present invention, can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of micro-organisms can be brought about by various antibacterial and anti-fungal agents, for example, parabens, chlorobutanol, phenol, sorbic acid, thimerosal, and the like. In many cases, it will be preferable to include isotonic agents, for example, sugars or sodium chloride.

The active compounds may be formulated for parenteral administration, e.g., formulated for injection via the intravenous, intramuscular, subcutaneous, intratracheal or even intraperitoneal routes. The preparation of an aqueous composition that contains the therapeutic compound as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified. Prolonged absorption of the injectable compositions can be brought about by the use in the compositions of agents delaying absorption, for example, aluminum monostearate and gelatin.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of micro-organisms, such as bacteria and fungi.

Solutions of the active compounds as free bases or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of micro-organisms.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more or highly concentrated solutions for intramuscular injection is also contemplated. In this regard, the use of DMSO as solvent is preferred as this will result in extremely rapid penetration, delivering high concentrations of the active peptide, peptides or agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose.

These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermolysis fluid or injected at the proposed site of infusion (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g.: inhalants and the like, which administer the active ingredients by aerolization; tablets or other solids for oral administration; time release capsules; and any other form currently used, including cremes, lotions and even mouthwashes.

Therapeutic formulations in accordance with the present invention may also be reconstituted in the form of inhalants which may contain the compound alone, or in conjunction with other agents, such as, e.g., pentamidine.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

REFERENCES

Berggren, P. O., and Larsson, O. (1994) Ca2+ and pancreatic B-cell function. Biochem. Soc. Trans. 22, 12-18.

Ebina, Y., Ellis, L., Jarnagin, K., Edery, M., Graf, L., Clauser, E., Ou, J. H., Maslarz, F., Kan, Y. W., Goldfine, I. D., Roth, R. A., and Rutter, W. J. (1985) The human Insulin Receptor cDNA: the structural basis for hormone-activated transmembrane signalling. Cell 40, 747-758.

Flier, J. S. (1996) Chapter 15; The Insulin Receptor. Diabetes Mellitus, Lippincott-Raven Publishers, Philadelphia.

Herz, J., and Gerard, R. D. (1993) Adenovirus-mediated transfer of low density lipoprotein receptor gene acutely accelerates cholesterol clearance in normal mice. Proc. Natl. Acad. Sci. USA 90, 2812-2816.

Kulkarnl, R. N., Bruning, J. C., Winnay, J. N., Postic, C., Magnuson, M. A., and Kahn, C. R. (1999) Tissue-specific knockout of the Insulin Receptor in pancreatic □ cells creates an insulin secretory defect similar to that of type 2 diabetes. Cell 96, 329-339.

Leibiger, I. B., Walther, R., Pett, U., and Leibiger, B. (1994a) Positive and negative regulatory elements are involved in transcriptional control of the rat glucokinase gene in the insulin producing cell line HIT M2.2.2. FEBS Letters 337, 161-166.

Leibiger, B., Walther, R., and Leibiger, I. B. (1994b) The role of the proximal CTAAT-box of the rat glucokinase upstream promoter in transcriptional control in insulin-producing cells. Biol. Chem. Hoppe-Seyler 375, 93-98.

Leibiger, I. B., Leibiger, B., Moede, T., and Berggren, P. O. (1998a) Exocytosis of insulin promotes insulin gene transcription via the Insulin Receptor/PI-3 kinase/p70 s6 kinase and CaM kinase pathways. Mol. Cell 1, 933-938.

Leibiger, B., Moede, T., Schwarz, T., Brown, G. R., Köhler, M.,

Leibiger, I. B., and Berggren, P. O. (1998b) Short-term regulation of insulin gene transcription by glucose. Proc. Natl. Acad. Sci. USA 95, 9307-9312.

Leibiger, B., Wahlander, K., Berggren, P. O., and Leibiger, I. B. (2000) Glucose-stimulated insulin biosynthesis depends on insulin-stimulated Insulin gene transcription. J. Biol. Chem. 275, 30153-30156. JBC published Jul. 25, 2000 as 10.1074/jbc.M005216200

Levy-Toledano, R., Caro, L. H. P.,.Accili, D., and Taylor, S. I. (1994) Investigation of the mechanism of the dominant negative effect of mutations in the tyrosine kinase domain of the Insulin Receptor. EMBO J. 13, 835-842.

Moede, T., Leibiger, B., Pour, H. G., Berggren, P. O., and Leibiger, I. B. (1999) Identification of a nuclear localization signal, RRMKWKK, in the homeodomain transcription factor PDX-1. FEBS Letters 461, 229-234.

Moitoso de Vargas, L., Sobolewski, J., Siegel, R., and Moss, L. G. (1997) Individual □ cells within the intact islet differently respond to glucose. J. Biol. Chem. 272, 26573-26577.

Russell, P. R (1985) Gene 40, pp. 125-130.

Sambrook, J., Fritsch, E. F., Maniatis, T., (1989) Molecular Cloning, A Laboratory Manual Second Edition. Cold Spring Harbor Laboratory Press.

Sharma, A., Fusco-DeMane, D., Henderson, E., Efrat, S. and Stein, R. (1995) The role of the insulin control element and RIPE3b1 activators in glucose-stimulated transcription of the insulin gene. Mol. Endocrinol. 9, 1468-1476.

Taylor, S. I. (1999) Deconstructing type 2 diabetes. Cell 97, 9-12.

Ullrich, A., Bell, J. R., Chen, E. Y., Herrera, R., Petruzzelli, L. M., Dull, T J., Gray, A., Coussens, L., Liao, Y. C., Tsubokawa, M. Mason, A., Seeburg, P. H., Grunfeld, C., Rosen, O. M., and Ramachandran, J. (1985) Human Insulin Receptor and its relationship to the tyrosine kinase family of oncogenes. Nature 313, 756-761.

Wang, X., Freeman, M., and Seed, B. (1998) Free inverted terminal repeat ends are required for efficient generation of recombinant adenoviral vectors. 1st Annual Meeting of the American Society of Gene Therapy, Seattle, Wash., May 28-31, #503.

Wang X, Appukuttan B, Ott S, Patel R, Irvine J, Song J, Park J H, Smith R, Stout J T (2000) Efficient and sustained transgene expression in human corneal cells mediated by a lentiviral vector.

Gene Ther, Feb;7(3):196-200

Watada, H., Kajimoto, Y., Umayahara, Y., Matsuoka, T., Kaneto, H., Fujitani, Y., Kamada, T., Kawamori, R., and Yamasaki, Y. (1996) The human glucokinase gene beta-cell-type promoter: an essential role of insulin promoter factor 1/PDX-1 in its activation In HIT-T15 cells. Diabetes 45, 1478-1488.

White, M. F., and Kahn, C. R. (1994) The insulin signaling system. J. Biol. Chem. 269, 1-4.

FIGURE LEGENDS

FIG. 1. Effect of glucose on βGK mRNA steady state levels, transcription initiation and mRNA stability.

(A) Elevation of βGK mRNA steady state levels in isolated islets after stimulation with 16.7 mM glucose (15 min). RNA was prepared 60 min after start of stimulation. Amounts of βGK and β-actin mRNA were quantified by comparative RT-PCR. The values of βGK mRNA were normalized to β-actin mRNA and are presented as percentages of mRNA levels of the non-stimulated control (given as 100%).

(B) Dynamics of βGK mRNA stability in islet cells at 3 mM glucose (filled squares) and after stimulation with 16.7 mM glucose for 15 min (open squares). Actinomycin D (5 μg/ml) was present all the time under non-stimulated conditions (■), whereas in case of stimulation (□) the inhibitor was added 45 min after start of stimulation. βGK mRNA values were normalized to β-actin mRNA and are presented as percentages of mRNA levels of the non-stimulated control at minute 0 (given as 100%).

(C,D) Dynamics of βGK transcription initiation in response to glucose stimulation in HIT cells (C) and isolated islets (D). Transcription initiation was studied by nuclear run-off analysis. Elevation of RNA levels in stimulated cells is shown as percentage of RNA levels of the non-stimulated control (given as 100%). The values of βGK mRNA were normalized to amounts of β-actin mRNA. All data are shown as mean values ±S.E. (n=3).

Figure 2D:
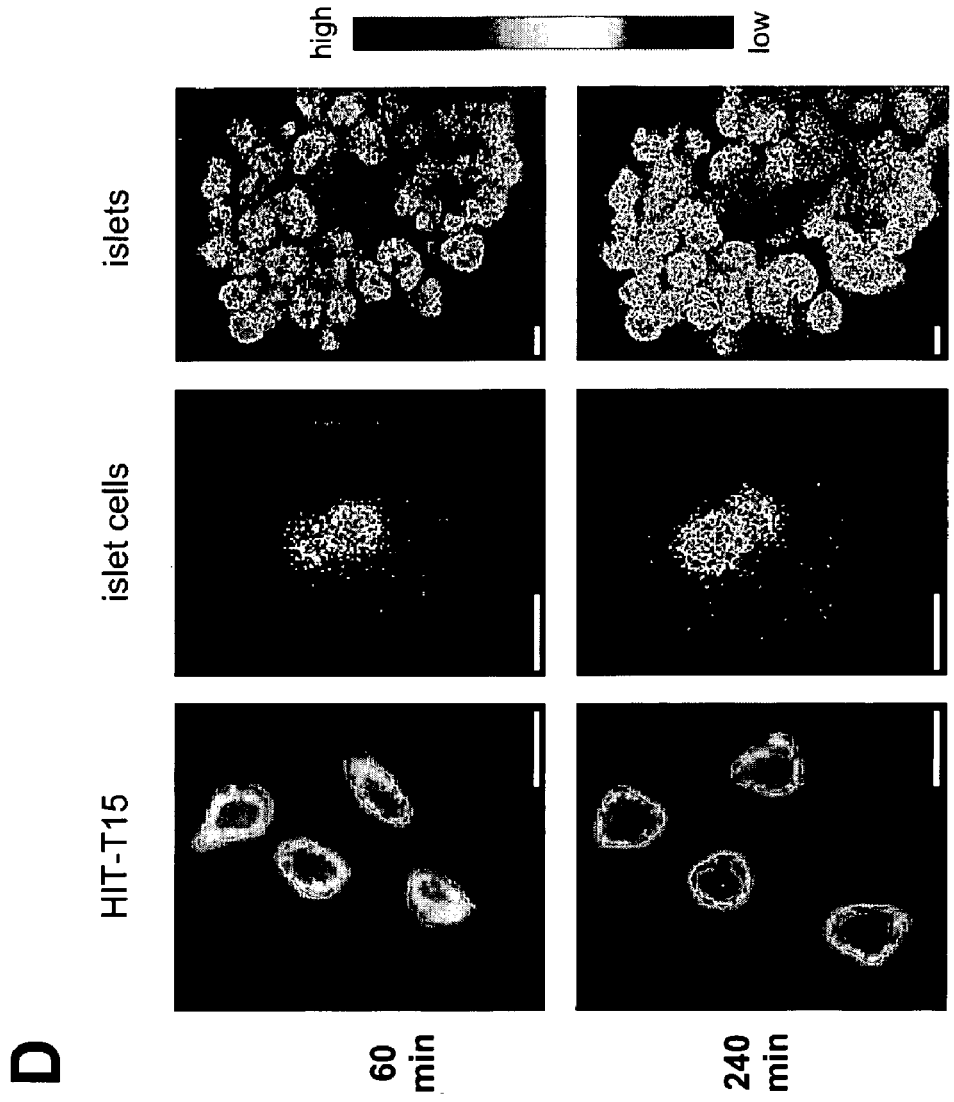

FIG. 2. On-line monitoring of glucose-stimulated βGK promoter-driven GFP expression in transfected HIT-T15 cells (A), islet cells (B) and in whole islets (C).

(A,B) HIT cells and islet cells were transfected with prβ-GK.GFP (rβGK) or with pRcCMV.GFP (CMV) as control and stimulated with 16.7 mM glucose for 15 min. Non-stimulatory glucose concentrations for HIT cells and islet cells were 0.1 mM and 3 mM, respectively. On-line monitoring of GFP expression was performed by digital imaging fluorescence microscopy. Data are shown as mean values ±S.E. (n=10).

(C) Isolated islets were transduced with either Ad.rβ-GK.GFP (rβGK) or Ad.CMV.GFP (CMV) and stimulated for 15 min with 16.7 mM glucose. Non-stimulatory glucose concentration for islets was 3 mM. On-line monitoring of GFP expression was performed by laser-scanning confocal microscopy. Data are shown as mean values ±S.E. (n=3).

(D) Representative images of HIT cells (n=40), islet cells (n=40) and islets (n=3) are shown 60 and 240 min after start of glucose stimulation. Images were obtained by digital imaging fluorescence microscopy (HIT cells and islet cells) and by laser-scanning confocal microscopy (islets). The pseudocolor images were created by converting the original 'gray-scale' data using ISee-software; the fluorescence increases from blue to red. The scale bars represent 10 μm.

FIG. 3. Effect of secretagogues and voltage-dependent L-type $Ca^{2+}$ channel blockers on endogenous βGK mRNA levels and βGK promoter-driven GFP expression.

(A) Elevation of endogenous βGK mRNA levels in cultured pancreatic islets in response to stimulation for 5 min with either 50 mM KCl (KCl) or 1 μM glibenclamide (glib) at 3 mM glucose. Amounts of βGK mRNA are presented as percentage of mRNA levels of the non-stimulated control (given as 100%). Data are shown as mean values ±S.E. (n=3). (B) Elevation of endogenous βGK mRNA levels in islets cells in response to stimulation for 15 min with 16.7 mM glucose with or without 10 μM of the L-type $Ca^{2+}$ channel blocker nifedipine (nif). Amounts of βGK mRNA are presented as percentage of mRNA levels of the non-stimulated control (given as 100%). Data are shown as mean values ±S.E. (n=3). Nifedipine was given 30 min prior to stimulation and kept throughout stimulation. (C,D) On-line monitoring of βGK promoter-driven GFP expression in transfected HIT-T15 cells (C) and islet cells (D). Islet cells and HIT cells were transfected with prβGK.GFP (βGK) or with pRcCMV.GFP (CMV) as control and stimulated with 50 mM KCl or 1 μM glibenclamide as described in Experimental Procedures. Data are shown as mean values ±S.E. (n=8).

FIG. 4. Insulin-stimulated βGK gene transcription.

(A,B) Effect of increasing concentrations of insulin added to the RPMI 1640 culture medium for 5 min, on (A) endogenous βGK mRNA levels in isolated pancreatic islets and on (B) βGK promoter-driven GFP expression and insulin promoter-driven DsRed expression in transfected HIT-T15 cells.

(A) Amounts of βGK mRNA are presented as percentage of mRNA levels of non-stimulated control (given as 100%). Quantification of (prepro)insulin mRNA was performed by comparative RT-PCR. Data are shown as mean values ±S.E. (n=3).

(B) On-line monitoring of βGK promoter-driven GFP expression and insulin promoter-driven DsRed expression. HIT cells were co-transfected with prβGK.GFP (white bars) and prIns1.DsRed (black bars) and stimulated for 5 min with the indicated amounts of exogenous Insulin. GFP- and DsRed-fluorescence was monitored from the same cells by digital imaging fluorescence microscopy as described in Experimental Procedures. Data are presented as the ratio of fluorescence obtained at minutes 240 and 60 and represent mean values ±S.E. (n=7).

(C-E) On-line monitoring of insulin-stimulated βGK promoter-driven GFP expression in transfected HIT-T15 cells (C), islet cells (D) and in transduced islets (E).

(C,D) HIT cells and islet cells were transfected with prβ-GK.GFP (rβGK) or with pRcCMV.GFP (CMV) as control and stimulated with 5 mU insulin/ml for 5 min. Non-stimulatory conditions for HIT cells and islet cells were 0.1 mM and 3 mM glucose, respectively. On-line monitoring of GFP expression was performed by digital imaging fluorescence microscopy. Data are shown as mean values ±S.E. (n=10).

(E) Isolated islets were transduced with either Ad.rβ-GK.GFP (rβGK) or Ad.CMV.GFP (CMV) and stimulated for 5 min with 5 mU insulin/ml. Non-stimulatory conditions for islets were 3 mM glucose. On-line monitoring of GFP expression was performed by laser-scanning confocal microscopy. Data are shown as mean values ±S.E. (n=3).

FIG. 5. Effect of various protein kinase inhibitors on insulin-and βGK promoter-activity and endogenous βGK mRNA levels.

Cells were stimulated for 5 min with 5 mU insulin/ml. Treatment with inhibitors lasted for 30 min prior to stimulation and throughout the time of stimulation. LY-25 μM LY294002, PD9-20 μM PD98059, PD1-10 μM PD169316, BIM-150 nM bisindolylmalemide I, rap-10 nM rapamycin, AC-400 nM autocamtide-2 related inhibitory peptide, HNMPA-100 μM HNMPA-$(AM)_3$.

(A) On-line monitoring of insulin promoter-driven (black bars) and βGK promoter-driven (white bars) GFP expression in transfected islet cells. Data are presented as the ratio of fluorescence obtained at minutes 240 and 60 and represent mean values ±S.E. (n=10).

(B) Amounts of βGK mRNA are presented as percentage of mRNA levels of non-stimulated control (given as 100%). Values for βGK mRNA were quantified by comparative RT-PCR and normalized to β-actin mRNA values. Data are shown as mean values ±S.E. (n=3).

FIG. 6. Effect of various protein kinase inhibitors on βGK promoter-driven GFP expression and insulin promoter-driven DsRed expression in co-transfected cells.

(A) HIT cells were co-transfected with prβGK.GFP (white bars) and prIns1.DsRed (black bars) and stimulated for 5 min with 5 mU insulin/ml. Treatment with inhibitors lasted for 30 min prior to stimulation and throughout the time of stimulation. LY-25 μM LY294002, rap-10 nM rapamycin, AC-400 nM autocamtide-2 related inhibitory peptide, HNMPA-100 μM HNMPA-$(AM)_3$. GFP- and DsRed-fluorescence were monitored from the same cells by digital Imaging fluorescence microscopy as described in Experimental Procedures. Data are presented as the ratio of fluorescence obtained at minutes 240and 60 and represent mean values ±S.E. (n=13).

(B) Representative images (out of a total of 18) of insulin-stimulated HIT cells co-transfected with prβGK.GFP and prIns1.DsRed with and without treatment with rapamycin. Images show read-outs for GFP fluorescence (βGK.GFP) and for DsRed-fluorescence (rIns1.DsRed) from the same cell 60 and 240 min after start of stimulation. Images were obtained by digital imaging fluorescence microscopy and created by converting the original 'gray-scale' data using ISee-software. The fluorescence increases from blue to red. The scale bars represent 10 μm.

FIG. 7. Protein kinase B/c-Akt is activated in insulin producing cells by secreted insulin.

(A,B) Effect of stimulation with 16.7 mM glucose (A) or 5 mU insulin/ml (B) on the phosphorylation of PKB/c-Akt at Ser$^{473}$. Data are from a representative experiment performed a minimum of three times with similar results on HIT cells.

(C-E) Dynamics of PKB activities following stimulation with 16.7 mM glucose (C) or 5 mU insulin/ml in HIT cells (D). (E) Effect of inhibition of glucose-induced insulin secretion by the L-type Ca$^{2+}$ channel blocker nifedipine (nif) and of inhibition of insulin-signaling by HNMPA-(AM)$_3$ (HNMPA) on PKB activity obtained 10 min after start of stimulation with glucose and 2 min after start of stimulation with insulin. Activities of PKB are presented as percentage of the activity of the non-stimulated control (given as 100%). Data are shown as mean values ±S.E. (n=3).

FIG. 8. Role of PKB/c-Akt in insulin-stimulated insulin- and βGK-transcription.

HIT cells were co-transfected with prβGK.GFP (white bars), prIns1.DsRed (black bars) and either kinase-inactive mutant of PKBα, i.e. PKBαΔ308/437 (mock), wild type PKBα (PKB), wild type PDK1 (PDK1) or an antisense construct of PDK1 (PDK1antisense). Transfected cells were stimulated for 5 min with 5 mU insulin/ml and GFP- and DsRed-fluorescence were monitored on-line by digital imaging fluorescence microscopy. Data are presented as the ratio of fluorescence obtained at minutes 240 and 60 and represent mean values ±S.E. (n=8).

FIG. 9. Insulin-stimulated activation of insulin- and βGK-promoters is inhibited by different concentrations of PI3 kinase inhibitors in the same cell.

Effect of different concentrations of the independent PI3 kinase Inhibitors LY294002 (A) and wortmannin (B) on βGK promoter-driven GFP expression (white bars) and insulin promoter-driven DsRed expression (black bars) in co-transfected cells. Transfected HIT cells were stimulated for 5 min with 5 mU insulin/ml and GFP- and DsRed-fluorescence were monitored on-line in the same cells by digital imaging fluorescence microscopy. Data are presented as the ratio of fluorescence obtained at minutes 240 and 60 and represent mean values ±S.E. (n=7). Treatment with inhibitors lasted for 30 min prior to stimulation and throughout the time of stimulation.

FIG. 10. The role of Insulin Receptors.

(A) Effect of stimulation with either 16.7 mM glucose (15 min) or 5 mU insulin/ml (5 min) on endogenous insulin and βGK mRNA steady state levels in isolated pancreatic islets obtained from βIRKO mice (βIRKO) or control animals (wild type). RNA was prepared 60 min after start of stimulation. Amounts of insulin, βGK and β-actIn mRNA were quantified by comparative RT-PCR. The values of insulin and βGK MRNA were normalized to amounts of β-actin mRNA and are presented as percentages of mRNA levels of the non-stimulated islets (given as 100%). Data are shown as mean values ± S.E. (n=3). (B-D) On-line monitoring of βGK promoter-driven GFP expression (white bars) and insulin promoter-driven DsRed expression (black bars) in co-transfected HIT cells (B,C) or islet cells (B,D).

(B) Cells were co-transfected with prβGK.GFP and prIns1.DsRed and stimulated for 5 min with either 5 mU insulin/ml or 2.6 nM IGF-I. GFP- and DsRed-fluorescence was monitored on-line in the same cells by digital imaging fluorescence microscopy. Data are presented as the ratio of fluorescence obtained at minutes 240 and 60 and represent mean values ± S.E. (n=10). (C,D) Cells were co-transfected with prβGK.GFP and prIns1.DsRed and either expression constructs for wild type isoforms of Insulin Receptor A (HIR (A)), Insulin Receptor B (HIR(B)), or the M1153I-mutant of the respective receptor isoform, i.e. HIR(A)m and HIR(B)m, respectively. Transfected cells were stimulated for 5 min with 5 mU insulin/ml and GFP- and DsRed-fluorescence was monitored on-line in the same cells by digital imaging fluorescence microscopy. Data are presented as the ratio of fluorescence obtained at minutes 240 and 60 and represent mean values ± S.E. (n=10).

FIG. 11. Effect of selective inhibition of Insulin Receptor isoforms.

(A,B) Effect of antibodies that block signaling through A and B type Insulin Receptors (αIR(AB)), through B type Insulin Receptors (αIR(B)) and through IGF-I receptors (αIGF-1R) on insulin-stimulated βGK promoter-driven GFP expression (white bars) and insulin promoter-driven DsRed expression (black bars) in co-transfected HIT cells (A) or islet cells (B). Transfected cells were stimulated for 5 min with 5 mU insulin/ml. GFP- and DsRed-fluorescence were monitored on-line in the same cells by digital imaging fluorescence microscopy. Cells were incubated with 0.67 µg/ml of the respective antibodies 30 min prior to stimulation and throughout stimulation. Data are presented as the ratio of fluorescence obtained at minutes 240 and 60 and represent mean values ± S.E. (n=10).

(C) Effect of inhibited insulin signaling via the B type receptor by αIR(B) on insulin-stimulated elevation of βGK mRNA steady state levels following stimulation with either 16.7 mM glucose (15 min) or 5 mU insulin/ml (5 min). (D) Effect of inhibited insulin signaling by αIR(AB) on insulin-stimulated elevation of βGK mRNA steady state levels following stimulation with 5 mU insulin/ml (5 min). (C,D) RNA was prepared 60 min after start of stimulation. Amounts of βGK and β-actin mRNA were quantified by comparative RT-PCR. The values of βGK mRNA were normalized to amounts of β-actin mRNA and are presented as percentages of mRNA levels of the non-stimulated control (given as 100%). Data are shown as mean values ±S.E. (n=3).

FIG. 12. Molecular mechanisms involved in the selective insulin signaling via IR-A and IR-B.

(A) Distribution of IR-A~GFP (green) and IR-B~DsRed (red) In HIT cells obtained by laser scanning confocal microscopy. Areas in yellow indicate co-localization of the two IR isoforms. This is a representative image out of a total of 25.

(B) PI3K activity In GFP-immunoprecipitates obtained from insulin-stimulated (150 nM insulin for 5 min) HIT cells overexpressing either IR-A~GFP (black bars) or IR-B~GFP (white bars). The amount of wortmannin included in the in vitro assay is indicated. Data are presented as mean values ±S.E. (n=3).

(C) Effect of overexpression of dominant negative p85 PI3K subunit, Δp85, on insulin-stimulated βGK promoter-driven GFP expression (white bars) and insulin promoter-driven DsRed expression (black bars) in co-transfected HIT cells. Data are presented as the ratio of fluorescence obtained at minutes 240 and 60 and represent mean values ±S.E. (n=10).

(D,E) Analysis of insulin-stimulated p70 s6 kinase and PKB activities in HIT (D) and HEK293 (E) cells following transfection with IR-A or IR-B. Cells were stimulated with insulin for 10 min and lysed after further 10 min. Data are represented as percentages of the non-stimulated, mock-transfected control, set as 100%, and presented as mean values ± S.E. (n=3).

FIG. 13. Selective activation of insulin and glucokinase gene transcription by selective insulin signaling via A and B type Insulin Receptors.

The scheme illustrates the coupling between insulin exocytosis and the activation of transcription of insulin and glucokinase genes. $[Ca^{2+}]_i$-cytosolic free $Ca^{2+}$, $p70^{s6k}$- p70s6 kinase, IRS-Insulin Receptor substrate, PI3 kinase*-PI3 kinase activity, which is different from that involved in insulin-stimulated insulin gene transcription.

Figure 14:
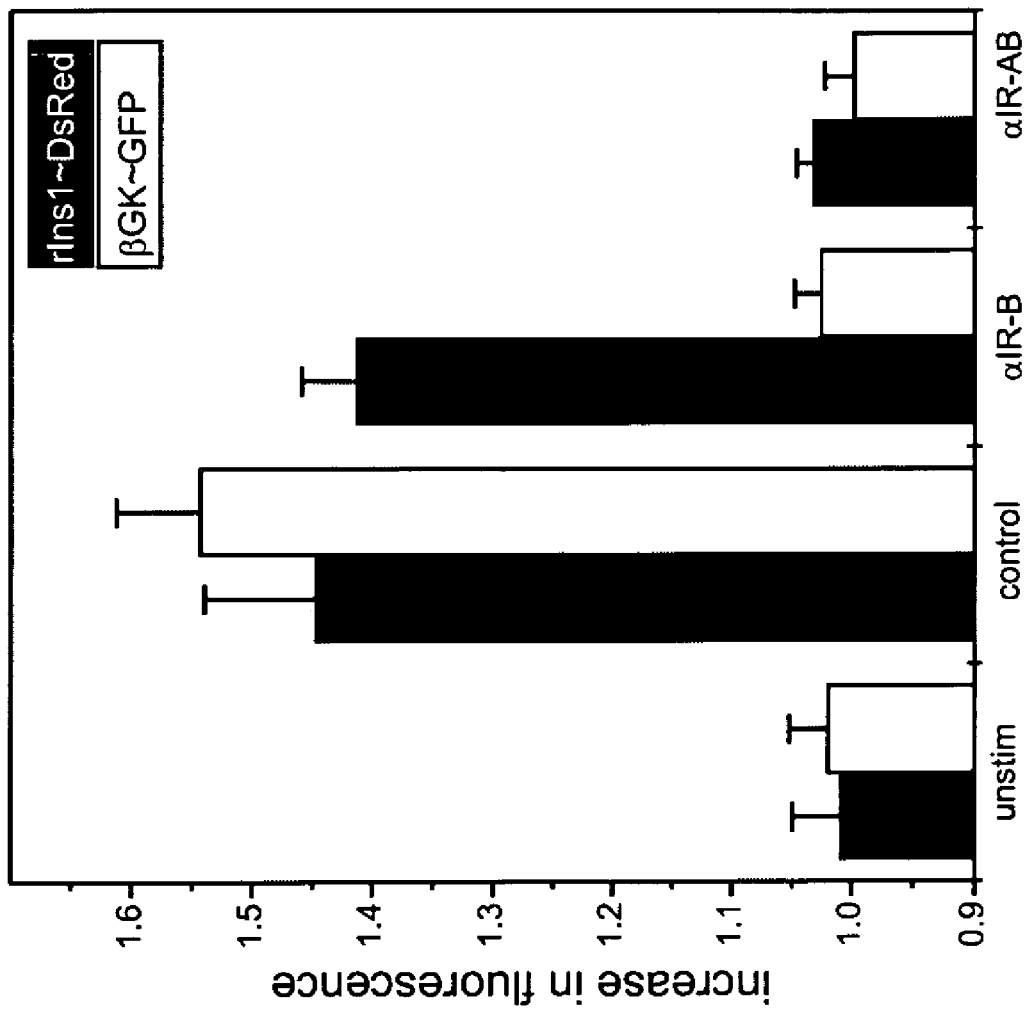

FIG. 14. The role of insulin receptors in gene transcription in human β-cells

Effect are displayed of antibodies that block signaling through insulin receptor A and B (αIR-AB) and through insulin receptor B (αIR-B) on insulin stimulated rat βGK promoter-driven GFP expression (open bars) and rat insulin-I promoter-driven DsRed expression (closed bars) in co-transfected human islet cells. Cells were incubated with 0.67 μg/ml of the respective antibodies 30 min prior to and throughout stimulation with 5 mU/ml insulin. Control cells were either not stimulated (unstim) or stimulated with 5 mU/ml insulin. Data are presented as the ratio of fluorescence obtained at minutes 240 and 60 and represent mean values ±S.E. (n=11).

Figure 15:
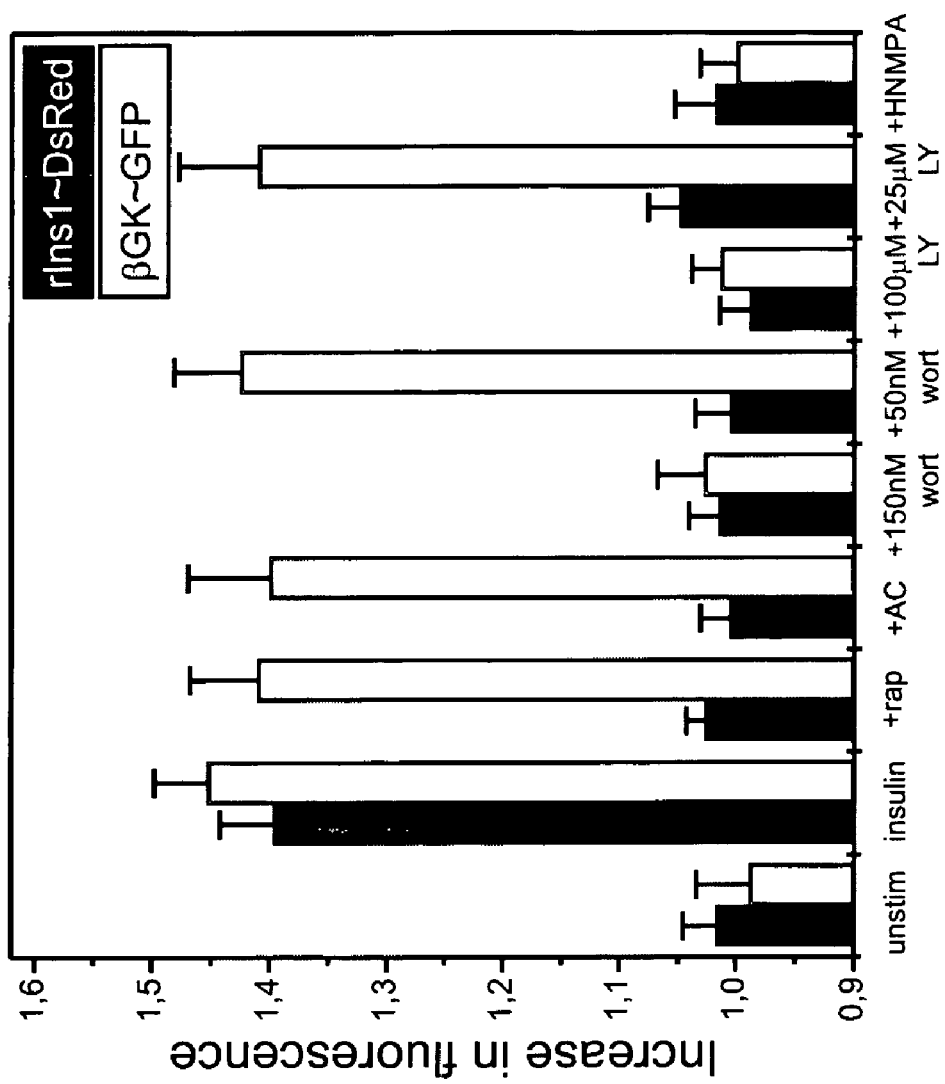

FIG. 15. Influence of various protein kinase inhibitors on gene transcription in human β-cells Effect of various protein kinase inhibitors on insulin stimulated βGK-promoter driven GFP expression (open bars) and insulin-promoter driven DsRed expression (closed bars) are demonstrated in co-transfected human islet cells. Cells were incubated with 10 nM rapamycin (p70s6k, rap), 400 nM autocamtide-2 related inhibitory peptide ($Ca^{2+}$/calmodulin dependent kinase II; AC), 50 nM or 150 nM wortmannin (PI3K; 50 nM or 150 nM wort), 25 μM or 100 μM LY 294002 (PI3K; 25 μM LY or 100 μM LY) or 100 μM HNMPA-$(AM)_3$ (IR tyrosine kinase; HNMPA) 30 min prior to and during stimulation with 5 mU/ml insulin. Controls cells were either not stimulated (unstim) or stimulated with 5 mU/ml insulin. Data are presented as the ratio of fluorescence obtained at minutes 240 and 60 and represent mean values ±S.E. (n=11).

EXAMPLES

Material and Methods

Inhibitors of protein kinases, bisindolyimaiemide I, PD98059, wortmannin, LY294002, rapamycin, HNMPA-$(AM)_3$ and autocamtide-2 related inhibitory peptide myristoylated and the L-type $Ca^{2+}$ channel blocker nifedipine were purchased from Calbiochem. Actinomycin D was from Sigma. Phosphatase inhibitor microcystin-LR and protein kinase inhibitor PD169316 were purchased from Alexis Biochemicals. Rabbit anti-Insulin Receptor alpha and Rabbit anti-Insulin Receptor B antibodies were from Biodesign. Mouse monoclonal IGF-IRα are from Pharmingen. Oligonucleotides were synthesized at Genset (France).

Expression Constructs

Construction of prIns1.GFP has been described earlier (Leibiger et al., 1998a). Vector prIns1.DsRed was generated by exchanging the EGFP-expression cassette versus the DsRed-expression cassette obtained from pDsRed1-1 (Clontech). Plasmid prβGK.GFP (i.e. prβGK-278.GFP) was generated by exchanging the CAT-SV40pA-expression cassette of prβGK-278.CAT (Leibiger et al., 1994a) versus the EGFP-bGHpA-expression cassette obtained from pRcCMVI.GFP (Moede et al., 1999). Site-directed mutagenesis to introduce the M1153I mutation into the Insulin Receptor cDNA was performed by employing the QuikChange Mutagenesis Kit (Stratagene). All vector constructions were verified by DNA sequence analysis. Constructs for expression of the human Insulin Receptor A and B types, pCMVHIR(A) and pCMVHIR(B) and the control plasmid pCMVstop were kindly provided by Dr. A. Ullrich (Max-Planck-Institute for Biochemistry, Martinsried, Germany). Expression constructs pCMV5.PKBα, pCMV5.PKBαΔ308/437, pCMV5.PDK1 and pCMV5.PDK1-antisense were kindly provided by Drs. P. Cohen and D. R. Alessi (MRC Phosphorylation Unit, University of Dundee, UK).

Replication-deficient adenovirus-based vectors Ad.rβ-GK.GFP and Ad.CMV.GFP were constructed as follows. Plasmid pAC.rβGK-278.GFP was obtained by subcloning the blunted Acc65-BamHI DNA fragment from prβGK.GFP into the blunted NotI-sites of the shuttle plasmid pAC.CMV.pLpA (Herz and Gerad, 1993). Plasmid pLEP.EGFP was constructed by inserting an EcoRI-NotI fragment containing the sequence for EGFP from pEGFP-N (Clontech) into EcoRI-NotI opened pLEPMV6, a derivative of pLEP3 (Wang et al., 1998). Ad.rβGK.GFP containing the rβGK.GFP transcription unit at the viral E1 region was obtained, as described previously by homologous recombination upon co-transfection of human embryonic kidney 293 cells (HEK293) with the viral genome-containing plasmid pJIM17 and pAC.rβGK-278.GFP (Moitoso de Vargas et al., 1997). Ad.CMV.GFP in which EGFP Is driven by CMV at the viral E1 region was produced by the two-cosmid system (Wang et al., 2000). Isolation by single plaque purification and amplification of Ad-constructs was performed as described in HEK293 cells (Moitoso de Vargas et al., 1997).

Cell Culture and Transfection

Insulin-producing HIT-T15 cells were obtained from ATCC. HIT cells were reported to show glucose responsiveness at subphysiological concentrations between 0.1 and 2 mM (Sharma et al., 1995). HIT cells were grown in RPMI 1640 medium supplemented with 100 units/ml penicillin, 100 μg/ml streptomycin, 2 mM glutamine and 10% fetal calf serum at 5% $CO_2$ and 37° C. Pancreatic islets were isolated from normally fed male Wistar rats and from mice by collagenase digestion. Isolated islets were incubated overnight at 5% $CO_2$ and 37° C. in RPMI 1640 medium, supplemented as described above. Transfection of HIT-T15 and islet cells was performed overnight by the lipofectamine technique in RPMI 1640 medium, without serum and antibiotics. For on-line monitoring, cells were grown and transfected on 24-mm glass coverslips. Following transfection, HIT cells were cultured for 12-18 h in RPMI 1640 medium containing 0.1 mM glucose, 10% fetal calf serum and supplemented as above. Before stimulation, islets and islet cells were incubated for 2 h in RPMI 1640 medium, supplemented as above but containing 3 mM glucose. All expression constructs were prepared using the Qiagen Plasmid Maxi Kit (Qiagen), except those used to produce the adenoviruses which where purified by ultracentrifugation via a CsCI-gradient (as described in Sambrook et al, 1989).

Islets were transduced with Ad.rβGK.GFP or Ad.CMV.GFP by incubating 50 islets with 1 ml virus-containing medium for 90 min at 37° C. and 5% $CO_2$. Following transduction, islets were washed 3 times with PBS and cultured further in RPMI 1640 medium. Islets were stimulated 40-72 h after transduction, as described below and analyzed by laser-scanning confocal microscopy.

Cultured islets, islet cells and HIT cells were stimulated with either 16.7 mM glucose for 15 min or 50 mM KCl, 1 μM glibenclamide or with various concentrations of insulin for 5 min at substimulatory glucose concentrations (3 mM for islets/islet cells and 0.1 mM for HIT cells). All experiments were performed in RPMI 1640 medium, supplemented as above. Protein kinase inhibitors, antibodies or nifedipine were added to the culture medium 30 min prior to stimulation and were kept in the medium throughout stimulation. After stimulation islets, islet cells and HIT cells were cultured further at substimulatory glucose concentrations (0.1 mM for HIT cells and 3 mM for islets and islet cells). For RNA-analysis, islets and cells were harvested 60 min after start of stimulation, if not indicated otherwise. For analysis of protein kinase activities or tyrosine phosphorylation, cells were harvested immediately following stimulation.

Nuclear Run-Off Analysis

Nuclear run-off analysis was performed as described previously (Leibiger et al.; 1998b), except that labeled RNA was hybridized to 2.5 µg cDNA of glucokinase, insulin, β-actin and control pBluescript-DNA, which were immobilized on nitrocellulose filters. For nuclear run-off analysis on islets, nuclei from 2000 islets per experiment were used. Data were analyzed by phosphorimaging. Values obtained for βGK mRNA were normalized by β-actin-mRNA values.

RNA Analysis Levels of βGK mRNA were analyzed by RNase-protection assays and comparative RT-PCR. For RNase-protection analysis, radiolabeled cRNAs were generated on the respective cDNA-containing linearized plasmids by employing the SP6/T7-ln vitro-transcription kit (Boehringer Mannheim) and $\alpha[^{32}P]$-CTP. Equal cpm of the labeled cRNA probes ($8\times10^4$cpm/µl final activity) were mixed with the total RNA In hybridization solution, Incubated for 5 mm at 90° C. and hybridized at 45° C. overnight. RNase protection was performed using the RPA II kit from Ambion. Quantification of the protected complexes was performed by phosphorimaging. Values obtained for µGK mRNAs were normalized to µ-actin-mRNA values. Levels of µGK mRNA were analyzed by RT-PCR using primers 5'-GT-TCCTACTGGAGTATGACC-3'(SEQ ID NO: 1) and 5'-CCTCCTCTGATTCGATGAAG-3'(SEQ ID NO: 2) for characterizing µGK mRNA in HIT cells and primers 5'-TG-GATGACAGAGCCAGGATGG-3'(SEQ ID NO: 3) and 5'-ACTTCTGAGCCTTCTGGGGTG-3'(SEQ ID NO: 4) for µGK mRNA in rat and mouse pancreatic islets and islet cells. Levels of µ-actin mRNA were analyzed by RT-PCR using primers 5'-AACTGGAACGGTGAAGGCGA-3'(SEQ ID NO: 5) and 5'-AACGGTCTCACGTCAGTGTA-3'(SEQ ID NO: 6). Total RNA obtained from either $10^6$ HIT cells or 15 pancreatic islets was reverse-transcribed using MMLV revertase. Aliquots of the generated cDNA were used for PCR mediated amplification using the RT-PCR Kit (Stratagene) and $\alpha[^{32}P]$-CTP for incorporation. PCR conditions were chosen which guaranteed the amplification of µGK and actin fragments within the linear range, as verified by testing various numbers of amplification cycles (10 to 35). PCR was performed in an Autogenell-thermocycler (Grant, UK), using a linked program (1 cycle: 5 mm 94° C., 5 min 54° C. and 2 mm 72° C. and 23 to 30 cycles: 1 min 94° C., 2 min 54° C. and 2 min 72° C.). PCR products were separated on a 6% polyacrylamide sequencing gel and analyzed by phosphorimaging. Quantification was performed with TINA-software 2.07d (Raytest), using co-amplified RT-PCR products for µ-actin as the internal standard.

Analysis of Tyrosine Phosphorylation of PKB/Akt

Phosphorylated PKB/c-Akt was analyzed by employing the PhosphoPlus Akt(Ser473) Antibody Kit (New England Biolabs) according to the manufacturer's instructions. Briefly, HIT cells were cultured as described above. Following stimulation with either 16.7 mM glucose or 5 mU insulin/ml for the time indicated, cells were washed with PBS and homogenized in lysis buffer containing 50 mM Tris-HCl (pH7.5), 50 mM NaF, 0.5 mM $Na_3VO_4$, 0.1 mM phenylmethylsulfonyl fluoride, 1 µg/ml aprotinin, 1 µg/ml pepstatin, 1 µg/ml leupeptin, 1 µM microcystin, 1% (v/v) Triton X-100, 10 mM sodium β-glycerophosphate, 0.1% (v/v) 2-mercaptoethanol, 5 mM $Na_4P_2O_7$, 1 mM EDTA, 1 mM EGTA. Following centrifugation of the lysate for 20 min at 14,000×g and 4° C., aliquotes of the supernatant containing 200 µg protein were separated by SDS-PAGE over a 7.5% polyacrylamide gel. Proteins were electro-transferred onto PVDF-membrane (Immobilon-P, Millipore) overnight at stabilized 125 mA. Immunoblotting was performed with either rabbit polyclonal Phospho-Akt(Ser473) antibody or with rabbit polyclonal Akt (Ser473) antibody and HRP-conjugated secondary antibodies. For detection the membrane was incubated with Lumi-GLO containing peroxide and exposed to X-ray film.

Analysis of PKB/Akt Activity

Analysis of PKB/Akt activity was performed employing the Akt1-PKBα e Immunoprecipitation Kinase Assay Kit (Upstate Biotech.) according to the manufacturer's instructions. Lysates of HIT cells containing 1 mg of protein were subjected to immunoprecipitation. The immunoprecipitate was used for PKB/Akt kinase assay using $\gamma[^{32}P]$-ATP and Akt/SGK-specific substrate peptide. Phosphorylated substrates were blotted onto phosphocellulose P81 paper and analyzed by LSC.

On-line Monitoring of GFP and DsRed Expression.

Detection of fluorescence by digital imaging fluorescence microscopy was performed as described previously (Leibiger et al., 1998a; Leibiger et al., 1998b). Briefly, transfected cells were grown on 24-mm glass coverslips. After stimulation the coverslips were placed into a perifusion chamber which was mounted on an inverted microscope (Zeiss Axiovert 135TV). Temperature was kept at 37° C. and the cells were perfused with RPMI 1640 medium. The objective lens used was a Zeiss-Fluar ×40/1.30 oil Imm Korr. Fluorescence imaging was performed with a cooled charged-coupled device camera (CH250 with KAF 1400, Photometrics, Tucson, Ariz.) connected to an imaging system (Inovision) with fluorescence excitation from a SPEX fluorolog-2 CM1T11I spectrofluorometer (Spex Industries). The following filter-settings were used: for $GFP_{s65T}$: excitation at 485 nm, a 505 nm dicroic mirror and an emission band-pass filter of 500-530 nm; for DsRed: excitation at 558 nm, a 565 nm dicroic mirror and a 580 nm long-pass filter for emission Detection of Fluorescence by Laser Scanning-Confocal Microscopy.

Laser-scanning confocal microscopy was performed as described in (Leibiger et al., 1998b) using a LEICA CLSM (Leica Lasertechnik GmbH) with the following settings: ×25/0.75 oil Leitz NPL Fluotar objective lens, excitation wavelength 488nm (Krypton/Argon Laser) and a band-pass emission filter from 500-540 nm. After stimulation the islet was placed into the perifusion chamber and fixed by a metallic mesh to stabilize the position of the islet during the experiment.

On-line monitoring was initiated 60 min following the start of stimulation and the 60-min value of GFP- or DsRed-fluorescence was set to 1.0. Cells to be monitored were chosen randomly at minute 60 from six fields of vision and fluorescence was monitored up to minute 240. By overlaying the fluorescence and phase-contrast images, the position of cells on the coverslip could be checked. Fluorescence intensity was calculated by using the ISee-software for UNIX (Inovision Corporation).

Example 1

Glucose activates glucokinase gene transcription via secreted insulin

Insulin, secreted upon glucose-stimulation, is a key factor in the up-regulation of insulin gene transcription (Leibiger et al. 1998a). The promoters of both the insulin gene and the βGK gene contain many similar cis-acting elements (Watada et al., 1996). To test whether transcription of βGK is regulated by similar mechanisms as the insulin gene, the role of glucose and insulin in regulation of βGK mRNA steady-state levels was investigated. Stimulation of cultured islets (FIG. 1A) or insulin-producing HIT-T15 cells with 16.7 mM glucose led to an increase in βGK mRNA levels 60 min following start of stimulation. This is similar in time course to the effect of glucose to stimulate insulin mRNA levels (Leibiger et al., 1998a, 1998b).

To define in more detail the dynamics of βGK mRNA, the half-life time, stability and transcriptional rate of the βGK mRNA pool was analyzed. As shown in FIG. 1B, the half-life time of βGK mRNA was approximately 60 min, and was not changed in the presence or absence of glucose (FIG. 1B). On the other hand, stimulation of HIT cells with 16.7 mM glucose led to an increase in βGK gene transcripts as early as 15 min and reached a maximum of transcriptional activity at 30 min in a nuclear run-off assay (FIG. 1C). This effect of glucose on βGK transcription initiation was also observed in normal pancreatic islets (FIG. 1D). Forty-five min after glucose stimulation, there was a 3-fold increase in βGK transcripts in primary pancreatic beta cells. To further corroborate these data, a reporter gene assay was established using the βGK promoter coupled to the green fluorescent protein (GFP) as the reporter gene (prβGK.GFP). The rat βGK promoter fragment up to nucleotide-278 was used since this had been shown to contain all cis-elements responsible for both glucose-stimulus-dependent and cell-type-specific transcriptional control. Using GFP as the reporter, allowed for monitoring stimulus-dependent βGK promoter activity online in single beta cells and cell clusters, thereby overcoming the limitations set by the amount of cells when working with primary beta cells. Moreover, employing replication-deficient adenoviral vectors as the vehicle for gene transfer enabled the inventors to monitor βGK promoter activity in the context of the intact pancreatic islet. As demonstrated in FIG. 2, stimulation with 16.7 mM glucose led to an increase in βGK-promoter driven GFP fluorescence in HIT cells (FIG. 2A,D), isolated primary pancreatic beta cells (FIG. 2 B,D), as well as in intact pancreatic islets (FIG. 2C,D). As with the nuclear run-off assay, the dynamics of the activation of βGK-promoter-driven GFP expression were similar, if not identical, to those of the glucose-stimulated insulin gene promoter (Leibiger et al., 1998a, 1998b).

To determine whether glucose metabolism per se or secreted insulin (upon glucose stimulation) is a requirement for the up-regulation of βGK gene transcription, the effect of insulin secretagogues on βGK mRNA steady-state levels and βGK promoter-driven GFP expression was further investigated. Insulin secretagogues, like KCl or the sulfonylurea compound glibenclamide, stimulates insulin secretion by depolarizing the beta cell plasma membrane and provoking the influx of extracellular $Ca^{2+}$ through voltage gated L-type $Ca^{2+}$ channels. This pathway circumvents the glucose-metabolism-dependent depolarization via the ATP-triggered closure of beta cell $K_{ATP}$-channels (reviewed in Berggren and Larsson, 1994). As shown in FIG. 3, stimulation with either 50 mM KCl or 1 μM glibenclamide for 5 min at substimulatory glucose concentrations led to an increase in βGK mRNA steady state levels (FIG. 3A) and to an elevation in βGK promoter-driven GFP expression (FIG. 3 C,D). Alternatively, preventing stimulus-induced insulin secretion by blocking the influx of extracellular $Ca^{2+}$ via L-type $Ca^{2+}$ channels using nifedipine as a pharmacological inhibitor, abolished the up-regulation of βGK mRNA levels (FIG. 3B).

Next the effect of exogenously administered insulin on βGK mRNA steady-state levels and βGK promoter-driven GFP expression was studied at substimulatory glucose concentrations (FIG. 4A-E). Addition of only 50 μU insulin per ml to fully supplemented culture medium was sufficient to evoke βGK mRNA levels in pancreatic islets (FIG. 4A). Interestingly, a more careful comparison of the necessary amounts of exogenous insulin to trigger promoter activities, revealed that instead of 5-10 μU insulin per ml of supplemented culture medium, as is the case with the insulin gene, the addition of 20 μU per ml was required to gain an effect on βGK promoter activation (FIG. 4B). As shown in FIG. 4C-E, stimulation with 5 mU insulin per ml of fully supplemented culture medium for 5 min led to an βGK promoter-driven increase in GFP fluorescence in HIT cells, isolated primary pancreatic beta cells as well as in intact pancreatic islets.

Taken together, these data support the view that the insulin gene and the beta cell transcription unit of the glucokinase gene are both stimulated by insulin that is secreted in response to glucose.

Example 2

Insulin-stimulated glucokinase gene transcription utilizes signal transduction, which is different from that of the insulin gene—protein kinases The careful studies of the present inventors on insulin-stimulated insulin gene transcription showed the involvement of phosphatidylinositol-3 kinase, p70 s6 kinase and $Ca^{2+}$/calmodulin dependent kinase(s) in the signaling cascade (Leibiger et al., 1998a). Previous data suggested that insulin- and βGK-promoters could bind the same transcription factors (Watada et al., 1996; Leibiger et al., 1994a, 1994b) and both genes did respond positively to many of the same stimuli (glucose, insulin, secretagogues) at the level of transcription, it was questioned whether both genes might be regulated by the same signaling pathway.

To test whether the same protein kinases that are involved in insulin-triggered insulin-gene transcription contribute to insulin-triggered transcription of βGK, the effect of pharmacological inhibitors on insulin-stimulated βGK promoter activity (FIG. 5) were studied. Insulin stimulation (5 mU/ml for 5 min at substimulatory glucose concentrations) was therefore combined with the co-treatment of islet cells and HIT cells with inhibitors of protein kinase C (PKC; 150 nM bisindolylmalemide I (BIM)), phosphatidylinositol-3 kinase (PI3K; 25 μM LY294002 (LY)), p70 s6 kinase (p70s6k; 10 nM rapamycin (rap)), MAP kinases Erk½ (20 μM PD98059 (PD9)) and p38/RK/SAPK2a+SAPK1/JNK (10 μM PD169316 (PD1)), Insulin Receptor tyrosine kinase (100 μM HNMPA-(AM)$_3$ (HNMPA)) and $Ca^{2+}$/calmodulin dependent kinase II (CaM KII; 400 nM autocamtide-2 related inhibitory peptide (AC)). The efficiency of these inhibitors was verified by the respective protein kinase assays in cell lysates of inhibitor-treated and non-treated cells following glucose/insulin stimulation (data not shown). In agreement with the data on insulin-stimulated insulin gene transcription, insulin-stimulated βGk transcription was not sensitive to inhibition of PKC, MAP kinases Erk½ and p38 but sensitive to inhibition of Insulin Receptor tyrosine kinase by HNMPA-(AM)$_3$ (FIG. 5). However, surprisingly, insulin-stimulated βGK transcription was not inhibited by LY294002 or by rapamycin, suggesting that signaling via PI3K/p70s6k is not involved. Moreover, while inhibition of CaM KII abolished insulin-stimulated insulin gene transcription, treatment with autocamtide-2 related inhibitory peptide altered neither insulin-stimulated βGK promoter activity (FIG. 5A) nor insulin-stimulated βGK mRNA steady-state levels (FIG. 5B).

To further confirm that insulin stimulates insulin gene transcription and βGK transcription using different signaling pathways, a technique was established that allowed monitoring insulin- and PGK-promoter activities simultaneously in the same cell. In addition to prβGK.GFP, an expression construct was generated wherein the rat insulin-I promoter (−410/+1 bp) controlled the expression of the red fluorescent protein DsRed, prIns1.DsRed. Because of their different excitation and emission profiles, the signals generated by the two fluorescent proteins can be measured directly in the same cell. Following co-transfectlon of islet cells and HIT cells with prβGK.GFP and prIns1.DsRed, insulin-stimulated insulin- and βGK-promoter activities were monitored as DsRed and GFP fluorescence, respectively. As shown in FIG. 6, stimulation with 5 mU/mi insulin led to an elevation in both DsRed- and GFP-fluorescence, as expected. This increase in fluorescence was abolished when the cells were treated with HNMPA-(AM)$_3$, thereby blocking the tyrosine kinase activity of Insulin Receptors (FIG. 6A). By combining insulin stimulation with pharmacological inhibitors of either PI3K (25 µM LY294002 (LY)), p70s6k (10 nM rapamycin (rap)) or CaM KII (400 nM autocamtide-2 related inhibitory peptide (AC)) it was shown that activation of the insulin promoter is abolished (no increase in DsRed fluorescence) (FIG. 6A,B). On the other hand, no effect on insulin-stimulated βGK promoter activity (increase in GFP fluorescence) was observed in the same cell (FIG. 6A). Thus, insulin activates the βGK promoter by employing a signaling pathway, which is different from that utilized by the insulin promoter.

Besides signaling via the MAP kinase and the PI3K/mTOR/p70s6k pathways, insulin has been shown to exert its effect via the activation of PKB(c-Akt). To test whether stimulation with either glucose or insulin leads to the activation of PKB in pancreatic beta cells the activated state of PKB, (Ser$^{473}$-phosphorylated PKB), was studied following stimulation with either 16.7 mM glucose or 5 mU insulin/ml. As shown in FIG. 7, PKB activation was observed 5 min following stimulation with 16.7 mM glucose (FIG. 7A) and 2 min following stimulation with 5 mU Insulin/ml at substimulatory glucose concentrations (FIG. 7B). These data were corroborated by measurements of PKB activities following stimulation with either 16.7 mM glucose (FIG. 7C) or 5 mU insulin per ml of fully supplemented culture medium (FIG. 7D). Prevention of glucose-induced insulin secretion by treatment of insulin-producing cells with the L-type Ca$^{2+}$ channel blocker nifedipine abolished glucose-induced activation of PKB, as did inhibition of insulin signaling by HNMPA-(AM)$_3$ (FIG. 7E). These data suggest that PKB is activated in response to glucose-stimulated insulin secretion. Because of the lack of a selective pharmacological inhibitor of PKB, its involvement in insulin-stimulated βGK gene transcription was tested by transiently overexpressing PKBα/c-Akt1. Whereas overexpression of PKBα had no effect on insulin-stimulated insulin gene transcription, it led to a more pronounced effect on insulin-stimulated βGK promoter-driven GFP expression (FIG. 8). According to the current view, insulin-stimulated PKB activation involves the phosphorylation of PKB by the phosphoinositol-dependent kinase 1, PDK1. Indeed, transient overexpression of PDK1 led to a more pronounced stimulation of insulin-triggered βGK promoter activity, whereas overexpression of the antisense transcript of PDK1 abolished the stimulatory effect of insulin on insulin-triggered βGK promoter activity (FIG. 8). Interestingly, the activation of PKB has so far been shown to be dependent on the activity of PI3K and therefore to be sensitive to the independent pharmacological inhibitors wortmannin and LY294002. Whereas treatment of insulin-producing cells with 25 µM LY294002 clearly abolished insulin-stimulated (5 mU insulin/ml) rat insulin-I gene promoter activity, it did not block insulin-stimulated rat βGK promoter activity (FIGS. 5A,B; 6A; 9A). When analyzing the effect of LY294002 on insulin-stimulated insulin- and βGK-promoter activity in cells co-transfected with prβGK.GFP and prIns1.DsRed in a dose-dependent manner, it was observed that LY294002 inhibited the two promoters at different concentrations. Whereas 25 µM LY294002 blocked insulin-stimulated insulin promoter activity, 100 µM LY294002 was necessary to completely abolish insulin-stimulated βGK promoter activity (FIG. 9A). The effect of wortmannin was similarly concentration dependent. Treatment of cells with 50 nM wortmannin was sufficient to inhibit insulin-stimulated insulin promoter activity, whereas 150 nM wortmannin was necessary to block insulin-stimulated βGK promoter activity (FIG. 9B). These data suggest that activation of PKB involves a phosphatidylinositol kinase, which is different from that contributing to insulin-stimulated insulin gene transcription. Interestingly, a difference in the sensitivity to both wortmannin and LY294002 has been reported between members of PI3K classes I and II, with a lower sensitivity for the latter.

Thus, these data indicate that insulin-stimulated βGK gene transcription occurs by signaling via PDK1/PKB, whereas insulin-stimulated insulin gene transcription is mediated via PI3K class Ia/p70s6k and CaM KII.

Example 3

Insulin signaling via A type Insulin Receptor activates insulin gene promoter whereas signaling via B type Insulin Receptor activates βGK promoter Previous data on insulin-stimulated insulin gene transcription (Leibiger et al., 1998a) favored signaling via Insulin Receptors but did not exclude the signaling via IGF-I receptors or possible hybrids of insulin and IGF-I receptors. The loss of insulin-effect, when treating cells with HNMPA-(AM)$_3$, an inhibitor of the Insulin Receptor tyrosine kinase, supported the idea that signaling via Insulin Receptors is crucial. Consequently, it was examined whether the expression of Insulin Receptors per se is an absolute requirement for insulin-stimulated insulin gene and βGK gene expression. Therefore, insulin and βGK mRNA levels were analyzed in response to glucose/insulin stimulation in isolated islets from βIRKO mice, a knock-out model that lacks the expression of Insulin Receptors, specifically in the pancreatic beta cell (Kulkarni et al., 1999). Stimulation with either 16.7mM glucose or 5 mU insulin/ml led to an increase in both endogenous insulin- and βGK-mRNA levels in islets of wild type mice, whereas no increase in insulin- and βGK-MRNA levels was observed in islets prepared from βIRKO mice (FIG. 10A). These data suggest that the expression of the Insulin Receptor in pancreatic beta cells is an absolute requirement to gain the stimulatory effect by insulin on both insulin- and βGK-gene expression and that signaling via IGF-I receptors is unlikely to be involved. This is consistent with the finding that activation of IGF-I receptors by stimulation with 2.6 nM IGF-I did not activate insulin promoter- or βGK promoter-driven reporter gene expression in insulin-producing cells (FIG. 10B).

Employing RT-PCR with subsequent DNA sequence analysis, the inventors had previously observed that insulin producing cells express both A and B type Insulin Receptors (Leibiger et al., 1998a). Transient overexpression of the A type receptor led to a more pronounced effect of insulin stimulation on insulin promoter activity, whereas overexpression of the B type receptor had no effect. To test a similar effect for insulin-stimulated βGK transcription islet cells and HIT cells were co-transfected with prβGK.GFP and prIns1.DsRed in combination with either the A or B type Insulin Receptor. Surprisingly, it was found that overexpression of the B type receptor (HIR(B)) led to a pronounced activation of the βGK promoter while overexpression of the A type receptor (HIR(A)) had no effect (FIG. 10C,D). Furthermore, overexpression of an inactive B type receptor mutant (HIR(B)m), described as M1153I (Levy-Toledano et al., 1994), did not lead to a further effect on βGK promoter-driven GFP expression (FIG. 10C,D).

To further test the Involvement of the B type Insulin Receptor in insulin-stimulated βGK promoter activation islet cells and HIT cells were treated with an anti-B receptor antibody, prior to glucose/insulin stimulation. This antibody selectively binds to the α-chain of B type receptors and therefore selectively blocks insulin binding to the B type receptor and signalling via B type receptors. Employing co-expression of prβGK.GFP and prIns1.DsRed in the same cell, it was observed that treatment of co-transfected cells with the B type receptor-specific antibody (αIR(B)) abolished insulin-stimulated prβGK.GFP expression, whereas it did not affect insulin-stimulated prIns1.DsRed expression (FIG. 11A,B). In addition, treatment of insulin producing cells with αIR(B) abolished elevation of βGK mRNA levels following stimulation with either 16.7 mM glucose or 5 mU insulin/ml at substimulatory glucose concentrations (FIG. 11C). As expected, treatment of transfected cells with an antibody that blocks insulin signaling via both receptor isoforms (αIR (AB)) suppressed insulin-stimulated activation of βGK and insulin promoters, (no insulin-stimulated expression of GFP and DsRed) (FIG. 11A,B). Accordingly, treatment of insulin producing cells with this antibody also abolished insulin-stimulated elevation of βGK mRNA steady state levels (FIG. 11D). By contrast, treatment of transfected cells with an antibody that blocks signaling via IGF-I receptors (αIGF-1R) did not affect insulin-stimulated activation of βGK and insulin promoters (FIG. 11A,B).

These data indicate that insulin stimulates the insulin gene promoter through the A type Insulin Receptor whereas it stimulates the βGK gene promoter via the B type Insulin Receptor.

Example 4

Molecular mechanisms involved in the selective insulin signaling via IR-A and IR-B:

To understand the molecular mechanisms that underlie the selectivity in insulin signaling via the two IR isoformes, experiment 4 aimed to explain the different sensitivity for PI3K inhibitors observed between insulin-stimulated insulin- and βGK-promoter activation. One possible interpretation would be that the same PI3K is involved in the transcription of both genes but that a lower PI3K activity is sufficient to trigger the cascade that activates βGK gene transcription via PKB. If this is the case, inhibition of PI3K-mediated βGK transcription should require higher concentrations of wortmannin or LY294002 to be fully effectuated. This should also be reflected upon by an inverse relationship between required inhibitor concentration and sensitivity of the respective promoter activity to insulin. If the same PI3K is sufficient to lead to the activation of both insulin- and βGK-promoters, then the promoter activity which is least sensitive to the inhibitors, i.e. βGK, would be expected to require less insulin to become stimulated. As this is not the case, another interpretation is that the different sensitivity in vivo could be due to a different accessibility of the inhibitor for the same type of PI3K, as a result of a different distribution/localization of the two IR isoforms, or it could be due to the involvement of different classes of PI3K, exhibiting a different sensitivity to wortmannin and LY294002 as described for PI3K classes I and II versus class II. To test whether IR-A and IR-B exhibit a distinct distribution in vivo, both receptor isoforms were tagged with GFP and DsRed at the C-terminus of the β-subunit. Tagging both IR isoforms did not interfere with their physiological function, e.g. overexpression of the tagged IR isoform led to a pronounced insulin-effect on the respective promoter activity to the same extent as the untagged IR (data not shown). Whereas transient co-expression of the same, but differently tagged (IR-A~DsRed/IR-A~GFP and IR-B~GFP/IR-B~DsRed), IR isoform led to a complete co-localization (data not shown), co-expression of the differently tagged IR-A and IR-B in either combination (IR-A~DsRed/IR-B~GFP and IR-A~GFP/IR-B~DsRed) clearly showed IR isoforms that are not co-localized. This pattern of distinct IR isoform distribution was observed in insulin producing cells HIT (FIG. 12A), INS1 and MIN6, as well as in non-insulin producing cells HEK293 and COS7 (data not shown). To test whether the two IR isoforms do utilize different classes of PI3K, IR-A~GFP or IR-B~GFP were overexpressed in HIT cells and the sensitivity of PI3K activity to wortmannin in vitro following immunoprecipitation with GFP-antibodies was studied. Whereas the PI3K activity in the IR-A immunoprecipitate was inhibited by wortmannin in the lower nanomolar range, as typical for PI3K class I and III, the PI3K activity in the IR-B immunoprecipitate was only inhibited at higher concentrations (FIG. 12B), as described for PI3K class II. To test whether insulin-stimulated insulin gene transcription involves IR-A-mediated insulin signaling via PI3K class Ia, insulin-stimulation was combined with the transient overexpression of the dominant negative form of the PI3K class Ia adapter protein p85, i.e. Δp85. Whereas transient overexpression of Δp85 totally abolished insulin-stimulated insulin promoter activity, this approach had no effect on insulin-stimulated βGK promoter activation (FIG. 12C).

Taken together, these data suggest a selectivity in insulin signaling in insulin-producing cells via IR-A through PI3K class Ia and p70s6k on the one hand, and via IR-B through a different PI3K activity, very similar to that of class II, and PKB on the other.

When separately overexpressing IR isoforms in HIT cells, a more pronounced activation of p70s6k was observed in cells overexpressing IR-A in response to insulin stimulation, while cells overexpressing IR-B showed a trend towards a higher PKB activity (FIG. 12D). To test whether this effect is purely specific for the pancreatic β cell, both PKB and p70s6k activities were analysed in non-insulin producing HEK293 cells that were transiently overexpressing either IR-A or IR-B. Most interestingly, insulin-stimulated p70s6k activity was more pronounced in cells overexpressing IR-A, whereas insulin-stimulated PKB activity seemed to be tighter coupled with the overexpression of IR-B (FIG. 12E).

Example 5

Regulation of insulin stimulated insulin and glucokinase gene transcription in human beta cells The above described results for glucose/insulin-stimulated up-regulation of insulin and glucokinase (βGK) gene transcription were obtained in primary beta cells from mouse and rat and in insulinoma cell lines HIT-T15 (hamster), INS-1 (rat) and MIN6 (mouse). In order to test whether the described mechanisms involved in the stimulus-dependent up-regulation of the two genes are the same or different in human beta cells, the following experiments were performed on human islet cells.

First, it was demonstrated that stimulation with 5 mU/ml insulin for 5 min at sub-stimulatory glucose concentrations results in the up-regulation of βGK promoter-driven GFP and insulin promoter-driven DsRed expression.

To test, whether signaling via Insulin Receptors (IR) is required for the up-regulation of insulin- and βGK-promoter activity in human cells, transfected human islet cells were treated with blocking antibodies that either prevent signaling through both IR-A and I (αIR-AB) or that block selectively signaling through IR-B only (αIR-B). Treatment with AB abolished the insulin-stimulated up-regulation of both insulin- and βGK-promoter-driven expression of DsRed and GFP, respectively. However, selective inhibition of signaling via IR-B abolished only up-regulation of βGK promoter-driven GFP expression but did not affect the up-regulation of insulin promoter-driven DsRed expression in response to insulin stimulation (FIG. 14)

To test, whether in human beta cells the same or different protein kinases as compared to the rodent cell systems contribute to the up-regulation of insulin and βGK gene expression, inhibitors for CaM kinase II (autocamtide-2 related inhibitory peptide [AC]), p70s6k (rapamycin) and IR tyrosine kinase (HNMPA-(AM)3) were employed. Furthermore, the impact of two different concentrations of the PI3K inhibitors LY294002 and wortmannin, respectively, were studied in order to test whether different classes of PI3K are involved in the up-regulation of the insulin and βGK promoters by insulin in human beta cells. The experiments showed (FIG. 15), that insulin-stimulated insulin gene expression is sensitive to inhibition of CaM kinase II, p70s6k and is inhibited by low concentrations of wortmannin or LY 294002, indicating the involvement of class Ia PI3K. This, together with the data employing the IR antibodies, confirmed that insulin stimulated gene transcription is regulated through a pathway involving IR A/PI3K class Ia/p70s6k and CaM K II in human cells.

Only the inhibitor for the IR tyrosine kinase and higher concentrations of wortmannin or LY 294002 had an inhibitory effect on insulin-stimulated glucokinase transcription.

Together with the effect of the IR-B-antibody, as described above, these data demonstrate, that the up-regulation of βGK promoter activity by insulin involves a pathway that includes the IR-B and a PI3K class II in human beta cells.

The invention claimed is:

1. A method for identifying a test substance for the treatment of one or more of non-insulin dependent diabetes mellitus, beta cell dysfunction and peripheral insulin resistance comprising:
   a) culturing a transfected cell population that comprises reporter genes under the control of the insulin promoter and reporter genes under the control of the βGK promoter under conditions suitable for expression of the reporter genes, and contacting the transfected cells with a test substance;
   b) measuring the levels of reporter gene expression;
   c) identifying one or more positive test substances that increase the level of expression of the reporter genes under control of the βGK promoter and do not increase the level of expression of the reporter genes under control of the insulin promoter, and
   d) testing the one or more positive test substances for use in treating one or more of non-insulin dependent diabetes mellitus, beta cell dysfunction and peripheral insulin resistance.

2. The method of claim 1 wherein the cell population comprises a first sub-population of cells comprising reporter genes under the control of the insulin promoter and a second sub-population of cells comprising receptor genes under the control of the βGK promoter.

3. The method of claim 1, wherein the testing comprises testing positive test substances for use in treating non-insulin dependent diabetes mellitus.

4. The method of claim 1, wherein the testing comprises testing positive test substances for use in treating beta cell dysfunction.

5. The method of claim 1, wherein the testing comprises testing positive test substances for use in treating peripheral insulin resistance.

6. The method of claim 1 wherein the transfected cell population comprises cells selected from the group consisting of transfected isolated pancreatic islets cells or insulin-producing HIT-T15 cells.

7. The method of claim 1 wherein the transfected cell population comprises cells derived from a stable transfected pancreatic beta cell line.

8. The method of claim 1, wherein measuring reporter gene expression is performed by measuring of fluorescence of expressed reporter gene product.

9. The method of claim 1 wherein the transfected cell population comprises mammalian cells.

10. The method of claim 1 wherein the transfected cell population comprises human cells.

11. The method of claim 1 wherein the culturing is performed under non-stimulatory glucose concentrations.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
gttcctactg gagtatgacc                                            20

<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
cctcctctga ttcgatgaag                                            20

<210> SEQ ID NO 3
<211> LENGTH: 21
<212> TYPE: DNA
<213> ORGANISM: Artificial
<220> FEATURE:
<223> OTHER INFORMATION: Synthetic

<400> SEQUENCE: 3
tggatgacag agccaggatg g                                          21
```

```
<210> SEQ ID NO 4
<211> LENGTH: 21
<212> TYPE: DNA
<213> ORGANISM: Artificial
<220> FEATURE:
<223> OTHER INFORMATION: Synthetic

<400> SEQUENCE: 4
acttctgagc cttctggggt g                                               21

<210> SEQ ID NO 5
<211> LENGTH: 20
<212> TYPE: DNA
<213> ORGANISM: Artificial
<220> FEATURE:
<223> OTHER INFORMATION: Synthetic

<400> SEQUENCE: 5
aactggaacg gtgaaggcga                                                 20

<210> SEQ ID NO 6
<211> LENGTH: 20
<212> TYPE: DNA
<213> ORGANISM: Artificial
<220> FEATURE:
<223> OTHER INFORMATION: Synthetic

<400> SEQUENCE: 6
aacggtctca cgtcagtgta                                                 20
```